(12) United States Patent
Zhang et al.

(10) Patent No.: US 8,622,061 B2
(45) Date of Patent: Jan. 7, 2014

(54) IMPLANTED SOFT PALATE SUPPORT AND IMPLANTATION METHOD

(76) Inventors: Xiangmin Zhang, Guangzhou (CN); Xing Zhou, Guangzhou (CN)

(*) Notice: Subject to any disclaimer, the term of this patent is extended or adjusted under 35 U.S.C. 154(b) by 380 days.

(21) Appl. No.: 13/060,716

(22) PCT Filed: Jun. 18, 2009

(86) PCT No.: PCT/CN2009/072328
§ 371 (c)(1),
(2), (4) Date: Feb. 25, 2011

(87) PCT Pub. No.: WO2010/022612
PCT Pub. Date: Mar. 4, 2010

(65) Prior Publication Data
US 2011/0174315 A1    Jul. 21, 2011

(30) Foreign Application Priority Data

Aug. 29, 2008 (CN) .......................... 2008 1 0198139
Nov. 17, 2008 (CN) .......................... 2008 1 0219169

(51) Int. Cl.
*A61F 5/56* (2006.01)
(52) U.S. Cl.
USPC ...................................................... 128/848
(58) Field of Classification Search
USPC ........... 128/848, 899; 600/9, 12; 623/9, 11.11
See application file for complete search history.

(56) References Cited

U.S. PATENT DOCUMENTS

| 6,955,172 B2* | 10/2005 | Nelson et al. ................. 128/848 |
| 2006/0060207 A1 | 3/2006 | Hegde et al. ................... 128/848 |
| 2006/0185680 A1* | 8/2006 | Bhat et al. ...................... 128/848 |

FOREIGN PATENT DOCUMENTS

| CN | 1391454 A | 1/2003 |
| CN | 101023891 A | 8/2007 |
| CN | 201005813 Y | 1/2008 |
| CN | 101385668 A | 3/2009 |

OTHER PUBLICATIONS

International Search Report, PCT/CN2009/072328, Sep. 17, 2009, 7 pages.

\* cited by examiner

*Primary Examiner* — Patricia Bianco
*Assistant Examiner* — Camtu Nguyen
(74) *Attorney, Agent, or Firm* — Morgan Lewis & Bockius LLP

(57) ABSTRACT

An implanted soft palate support and an implantation method are provided. The implanted soft palate support is a flat implant made of a material capable of being implanted into human tissues for a long time period, and includes a hard palate connecting end and a support. The hard palate connecting end has a connecting structure connected with a hard palate; the support is a flat implant capable of being inserted into a soft palate; and the hard palate connecting end is connected to the support. The implanted soft palate support can achieve the objectives of treating OSAHS and snoring by effectively lifting the collapsed soft palate during sleep and thereby reducing an upper airway obstruction condition. In particular, the soft palate support can be adjusted within a certain range to calibrate its shape and curvature event after the surgery, so as to achieve optimal treatment and comfort.

17 Claims, 16 Drawing Sheets

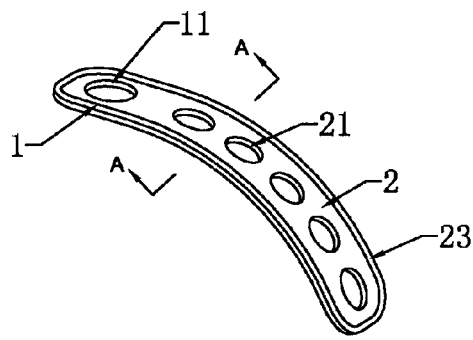
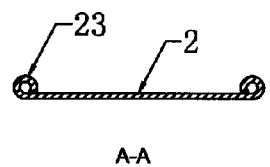
FIG. 20  FIG. 21
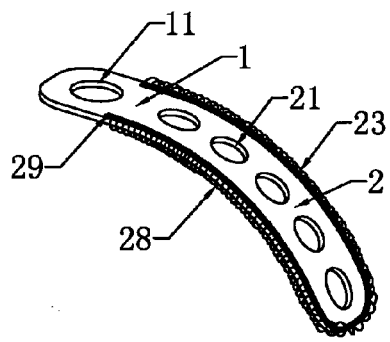
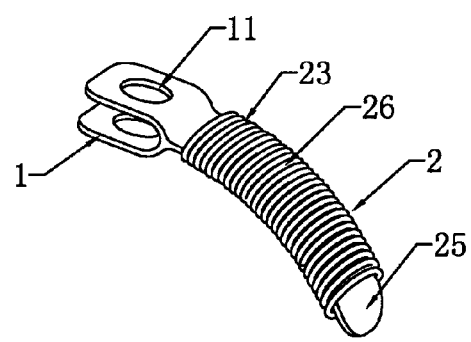
FIG. 22  FIG. 23
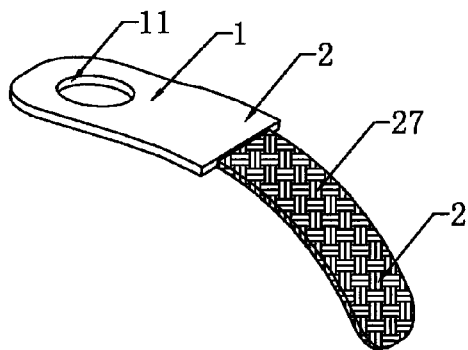
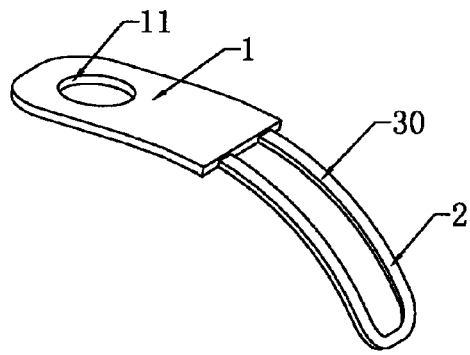
FIG. 24  FIG. 25

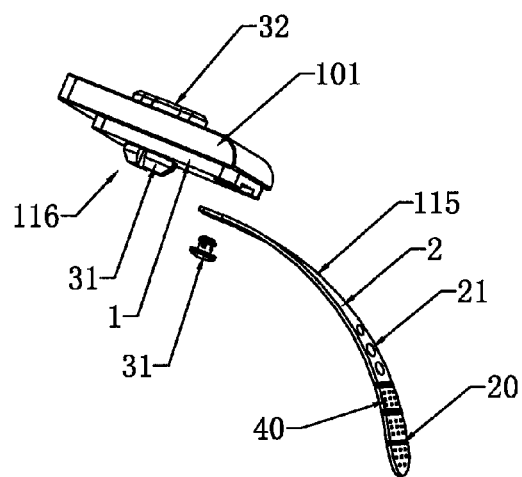
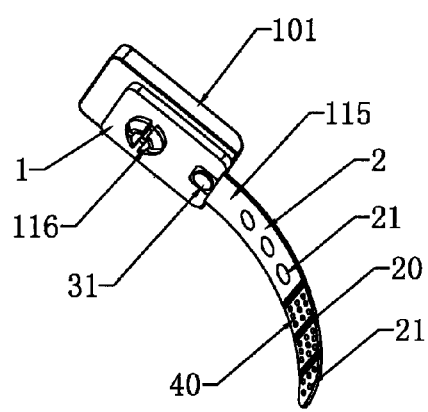
FIG. 49   FIG. 50
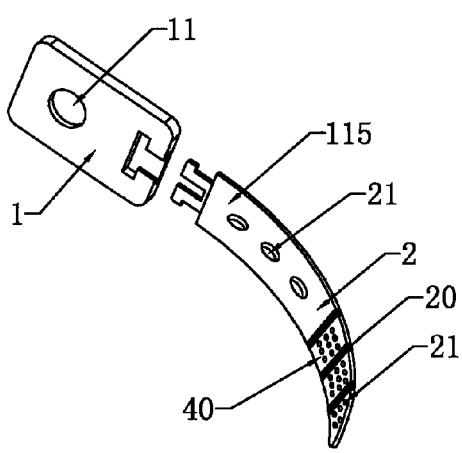
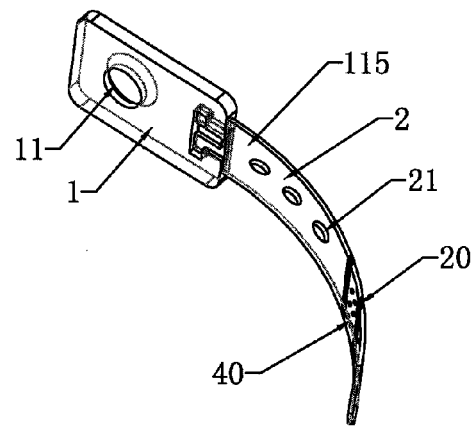
FIG. 51   FIG. 52

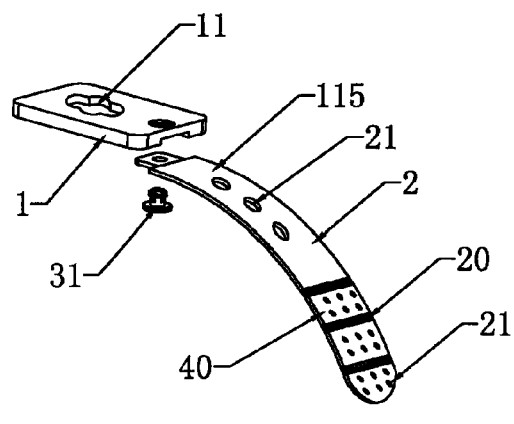
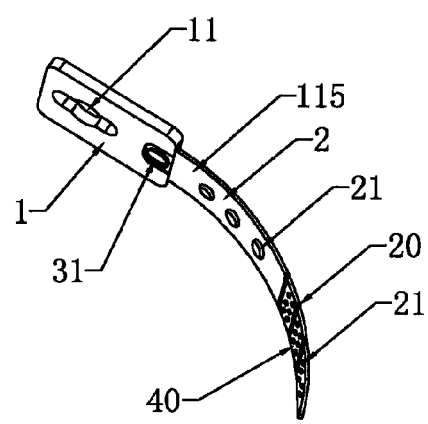
FIG. 53        FIG. 54
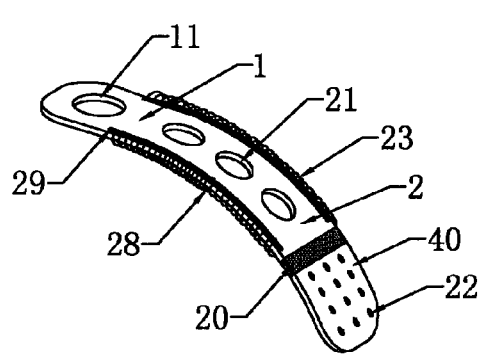
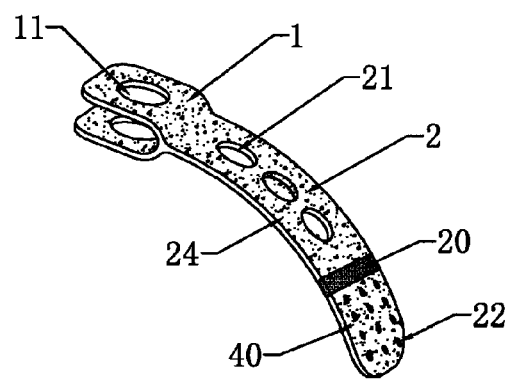
FIG. 55        FIG. 56

IMPLANTED SOFT PALATE SUPPORT AND IMPLANTATION METHOD

CROSS-REFERENCE TO RELATED APPLICATIONS

This Application is a United States National Stage Application filed under 35 U.S.C. §371 of PCT Patent Application Serial No. PCT/CN2009/072328 filed on Jun. 18, 2009 which claims benefit of and priority to Chinese Patent Application Serial No. 200810198139.6 filed on Aug. 29, 2008, and Chinese Patent Application Serial No. 200810219169.0 filed on Nov. 17, 2008, the disclosures of all of which are hereby incorporated by reference in their entirety.

BACKGROUND OF THE INVENTION

1. Field of the Invention

The present invention relates to an implanted soft palate support, and more particularly to an implanted soft palate support and an implantation method for treating adult obstructive sleep apnea/hypopnea syndrome (OSAHS).

2. Related Art

Adult OSAHS is a sleep breathing disorder with clinical features of snoring and apnea caused by upper airway collapse and obstruction during sleep. The morbidity of OSAHS is about 4% among adult men and about 2% among adult women even according to the lowest diagnosis criteria, and OSAHS presents a serious threat to the life and health of patients.

As for the pathogenesis of OSAHS, it is generally considered that the main cause is that, pharyngeal muscles for maintaining the upper airway open relax during sleep, resulting in soft tissue collapse and obstruction, and the plane of obstruction is usually located in the soft palate, tonsil, and tongue root. Many methods for treating OSAHS exist, which include two types, that is, non-surgical treatment and surgical treatment.

Methods of Non-Surgical Treatment Mainly Include:

1. Continuous Positive Airway Pressure (CPAP), in which a breathing machine capable of continuously generating a positive pressure air is closely connected with the nose and face of a patient via a nasal mask, so as to prevent collapse and obstruction of the soft tissues of the airway during sleep. Though the method has a good effect, it is difficult for approximately ⅔ of the patients to adapt to the machine, and they cannot sleep when wearing the machine.

2. Oral appliance. A device is placed in an oral cavity to move forward the mandible or pull forward the tongue, so as to enlarge the pharyngeal cavity and release the airway obstruction during sleep. The method has many types and produces a certain effect, but most patients cannot adapt to it. The oral appliance leads to irritation and foreign body sensation, causing that the user cannot fall asleep, and may have temporo-mandibular joint injury with long term use.

For example, International Application PCT/US2005/00139, Jan. 3, 2005, has disclosed a method and a device for relieving upper airway obstructions. The device includes a mouthpiece that is adapted to form a sealed cavity within a human mouth. The patient bites the device during sleep, so as to form the sealed cavity within the oral cavity. A negative pressure generator is connected with the device. For a patient suffering from OSAHS, the device is effective to pull the patient's tongue and/or soft tissues of the upper airway up and away from the posterior pharyngeal wall to reopen the airway.

Chinese Utility Model Patent ZL200620110299.7 has disclosed a tongue forward-moving device for treating OSAHS and snoring. The tongue forward-moving device includes a semi-lunar base, in which a semi-lunar upper-tooth receiving groove formed by front and rear flanges is provided at an upper portion of the base; an arc-shaped rear baffle is provided at a bottom portion of the base, and a tongue anchoring hole running through front and rear edges is provided in the center of the base; and an arc-shaped front baffle is provided at the bottom portion of the base, and a bracket for a lower front dentition is formed between the front and rear baffles. The tongue forward-moving device provides a die for being actively bitten by a patient with upper and lower front dentitions, so that the upper and lower muscles are subconsciously in a relatively tension state during sleep, thereby forming a stable fulcrum between the maxilla and mandible and the tongue forward-moving device. The tongue anchoring hole provides a comfortable anchor station for the apex of tongue, and regulates the tongue between the tongue anchoring hole and the hyoid bone, so as to maintain a smooth airway at the mouth and pharynx, thereby achieving the objective of treating OSAHS and snoring.

Many patents similar to the device disclosed in International Application PCT/US2005/00139, Jan. 3, 2005, and the tongue forward-moving device disclosed in Chinese Utility Model Patent ZL200620110299.7 exist. All the patents use the teeth as a supporting point in the oral cavity, and various appliances are designed to change the tension state or position of the tongue or the soft palate during sleep, so as to achieve the objective of treating OSAHS and snoring. These appliances are placed in the oral cavity and are bitten and fixed before sleep, but since persons continuously change the posture and mouth shape during sleep, the appliances often cannot function effectively. In addition, it is uncomfortable and inconvenient for the patients to use the appliances.

Methods of Surgical Treatment Mainly Include:

1. Radiofrequency ablation, which is also referred to as low-temperature plasma radiofrequency ablation, and is a minimally invasive surgical method. An electronic de is penetrated into the soft tissues which cause airway obstruction, such as the soft palate, tonsil, and tongue root, and is electrified to induce tissue coagulation, necrosis, fibrosis, and contraction by heating. The method has a certain therapeutic effect, is effective for a slight case, has a poor long-term efficacy, and is ineffective for serious patients.

2. Palatopharyngoplasty. Since Fujita improved the Palatopharyngoplasty of Ikematus, a Japanese scholar, into uvulopalatopharyngoplasty (UPPP) and introduced it to the US in 1981, various improved technologies based on UPPP, including Simmons method, Fairbanks method, Dickson method, Woodson method, Z-palatoplasty (ZPP), uvulopalatal flap (UPF), H-uvulopalatopharyngoplasty (H-UPPP) have been successively reported in literatures, which made a great contribution to symptom alleviation and recovery of OSAHS patients. Countless patients benefit from the surgical treatment solution. However, in terms of long-term effect, since the mucous membrane and soft palate tissue structure are excessively removed, functional muscles are injured, resulting in complications of nasal regurgitation during swallowing, rhinolalia aperta, and nasopharyngeal stenosis and atresia. It is the leading edge and focus for the research and development of OSAHS treatment technologies nowadays to develop a method and corresponding surgical instruments which create a smaller wound or perform surgical treatment in a minimally invasive manner.

3. Soft palate implantation. International Application PCT/US2002/007966, Mar. 14, 2002, has disclosed a braided palatal implant for snoring treatment. In the invention, the implant is embedded in the soft palate to alter the center of gravity of the soft palate when swinging with the air flow and alter the aerodynamic characteristics of the soft palate, so as to increase the critical air flow speed at the soft palate and the pharynx, thereby preventing snoring from occurring. However, the method fails to prevent OSAHS from occurring, for OSAHS occurs when the soft palate collapses and obstructs the upper airway, so that the method and the adopted braided implant cannot be used to treat OSAHS. For serious patients, the risk of OSAHS is increased because the weight at the swinging portion of the soft palate is increased.

Based on the above, though generating a certain effect, the existing technologies and methods for treating OSAHS and snoring still have many defects, and have a poor long-term effect. Therefore, it is necessary to develop a new method and design a new instrument to treat OSAHS and snoring, in which the new method should create a wound as small as possible, and the new instrument should be safe, effective, simple, and reliable.

SUMMARY OF THE INVENTION

Research reports and clinical experience indicate that, the relaxation and collapse of the soft palate portion is the main cause of snoring and OSAHS. The following implanted soft palate support for treating OSAHS and snoring is invented in view of the pathogenesis.

The present invention provides an implanted soft palate support, which is a flat implant made of a material capable of being implanted into human body for a long term, and includes: a hard palate connecting end having a connecting structure configured to be connected with a hard palate; and a support, being a flat implant capable of being inserted into a soft palate, in which the hard palate connecting end and the support are fixedly connected, or are detachably connected.

The connecting structure on the hard palate connecting end according to the present invention is selected from the following structures: a hole structure, a U-shaped clamp structure, a lock cache structure, a rivet-type structure, a self-expanding lock structure, and other connecting structures that facilitate fixation of the implanted soft palate support of the present invention to the hard palate.

The implanted soft palate support according to the present invention is selected from flat implants with the following structures: a strip-shaped structure, a plate-shaped structure, a bar-shaped structure, a net-shaped structure, and other flat objects.

The implanted soft palate support according to the present invention has a radian matching the curvature of the soft palate of the human body when it relaxes.

The implanted soft palate support according to the present invention has one or more through holes.

The implanted soft palate support according to the present invention has one or more convex steps or concave grooves.

The implanted soft palate support according to the present invention has a blunt edge formed by blunting.

The implanted soft palate support according to the present invention has a blunt edge coated with a flexible polymer material.

The implanted soft palate support according to the present invention has a coating capable of improving biocompatibility.

The hard palate connecting end and the implanted soft palate support according to the present invention are integrally manufactured.

The hard palate connecting end and the implanted soft palate support according to the present invention are assembled together such that the hard palate connecting end and the support may be disassembled or reassembled together.

The implanted soft palate support according to the present invention is a flat implant formed by a chip and a spring wire.

The implanted soft palate support according to the present invention is a flat implant braided by elastic wires.

The implanted soft palate support according to the present invention is made of the following materials capable of being implanted into the human body for a long term: a metal material, a medical polymer material, and a medical biodegradable material.

The metal material used for making the implanted soft palate support according to the present invention is one of titanium, a titanium alloy, a titanium-nickel shape memory alloy, a titanium-zirconium-niobium alloy, or other metal materials appropriate for medical use.

The implanted soft palate support according to the present invention includes an elastic module.

The elastic module of the implanted soft palate support according to the present invention is an object deformable under an external force and shape-recoverable after the external force is removed.

The elastic module of the implanted soft palate support according to the present invention is selected from the following structures: an elastic polymer material sheet or strip, a spring structure, a spring structure coated with a flexible polymer material, and other elastic flat objects.

The implanted soft palate support according to the present invention further includes a rigid module, and the rigid module is an object plastically deformable under an external force and not shape-recoverable after the external force is removed. The degree of curvature of the implanted soft palate support of the present invention may be adjusted after the rigid module deforms.

The implanted soft palate support according to the present invention further has one or more through holes or a convex-concave surface or rough surface supporting tissue penetration and growth.

The present invention further provides an implantation method of the implanted soft palate support, which includes: fixing the hard palate connecting end of the implanted soft palate support to a hard palate by using a fastener, and inserting the support of the implanted soft palate support into a soft palate.

The implanted soft palate support according to the present invention is inserted into the soft palate by a length equal to ⅕ to ⅘, and most preferably, ⅔ to ¾, of a total length of the soft palate.

The implanted soft palate support of the present invention is a flat object made of a material capable of being implanted into human body for a long term, and includes a hard palate connecting end and a support. The hard palate connecting end includes a connecting structure to be connected with a hard palate; the support is a flat implant capable of being inserted into a soft palate; and the hard palate connecting end is connected to the support. The implanted soft palate support can achieve the objectives of treating OSAHS and snoring by effectively lifting the collapsed soft palate during sleep and thereby reducing an upper airway obstruction. Clinical application has proved that, the method and implanted instrument of the present invention have the advantages of small wound, few complications, reliable efficacy, and great comfort for the patients, thereby realizing the objective of minimally invasive treatment. In particular, the soft palate support can be adjusted within a certain range to calibrate its shape and curvature even after the implantation surgery, so as to achieve optimal treatment and comfort.

BRIEF DESCRIPTION OF THE DRAWINGS

FIG. 20 is a schematic structural view of an implanted soft palate support of the present invention wherein an edge of the support is blunted;

FIG. 21 is an A-A cross-sectional view of FIG. 20;

FIG. 22 is a schematic structural view of an implanted soft palate support of the present invention wherein an edge of the support is blunted with a polymer material thread;

FIG. 23 is a schematic structural view of an implanted soft palate support of the present invention wherein an edge of the support is blunted with a titanium-nickel shape memory alloy wire;

FIG. 24 is a schematic structural view of an implanted soft palate support of the present invention wherein the hard palate connecting end and the support form a combined-type structure;

FIG. 25 is a schematic structural view of an implanted soft palate support of the present invention wherein the support is made of a memory alloy wire;

FIG. 36-1 is an enlarged view of part A of FIG. 36;

FIG. 36-2 is a B-B cross-sectional view of FIG. 36;

FIG. 49 is a schematic assembled view of a combined-type implanted soft palate support of the present invention wherein the support is assembled on top of the hard palate connecting end;

FIG. 50 is a schematic structural view of the combined-type implanted soft palate support of the present invention of FIG. 49 wherein the support is assembled behind the hard palate connecting end;

FIG. 51 is a schematic structural view of a combined-type implanted soft palate support of an engagement structure according to the present invention before being assembled;

FIG. 52 is a schematic structural view of FIG. 51 after being assembled;

FIG. 53 is a schematic structural view of a combined-type implanted soft palate support which is fixed using a fastener according to the present invention;

FIG. 54 is a schematic structural view of FIG. 53 after being assembled;

FIG. 55 is a schematic structural view of an implanted soft palate support of the present invention wherein an edge of the support is blunted with a polymer material thread in such a manner that holes or grooves are firstly cut at the edge of the support before blunting, and then the edge of the support is wrapped by a medical polymer material thread, so as to improve the edge effect of the support, increase the contact area of the edge, and achieve an objective of blunting the edge;

FIG. 56 is a schematic structural view of an implanted soft palate support of the present invention wherein the support is covered with a biocompatible coating so as to improve the biocompatibility of the support, and enhance the bonding force between the support and a soft palate;

The meanings of the serial numbers in the above drawings are as follows: 1 for hard palate connecting end, 2 for support, 11 for connecting structure connected with a hard palate, 20 for elastic module, 21 for through hole, 22 for convex-concave lines or rough surface, 23 for blunt edge, 24 for biocompatible coating, 25 for chip of the support, 26 for spring wire, 27 for braid, 28 for polymer material or polymer material thread, 29 for thread hole or groove, 30 for titanium-nickel shape memory alloy wire, 31 for bolt, 32 for nut, 40 for rigid module, 41 for small chamfer;

101 for hard palate, 102 for soft palate, 103 for nasopharynx, 104 for back end of the soft palate, 105 for epiglottis, 106 for esophagus, 107 for trachea, 108 for front end of the soft palate, 109 for supporting bone, 110 for nasal cavity, 111 for oral cavity, 112 for tongue, 113 for hard palate-soft palate junction, 114 for tongue root, 115 for implanted soft palate support of the present invention, 116 for fastener.

DETAILED DESCRIPTION OF THE INVENTION

In order to make the present invention more comprehensible, the pathogenesis of OSAHS is described with reference to FIG. 1 to FIG. 3.

Figure 1:
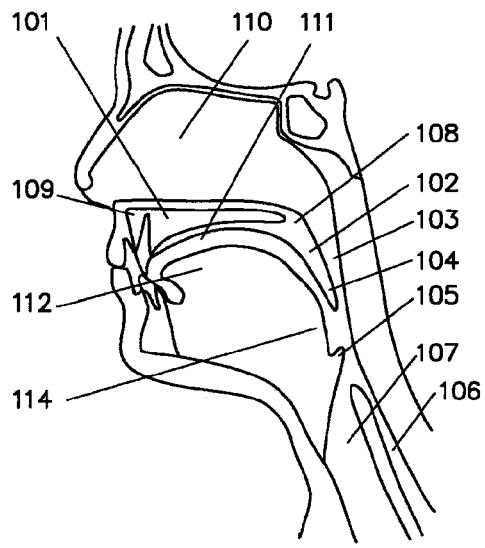
FIG. 1 is a cross-sectional side view of a human head during nasal breathing.

FIG. 1 is a cross-sectional side view of a human head during nasal breathing. When a human is breathing, the soft palate 102 naturally falls, the epiglottis 105 opens, and air may enter trachea 107 via nasal cavity 110 (or oral cavity 111, during mouth breathing).

Figure 2:
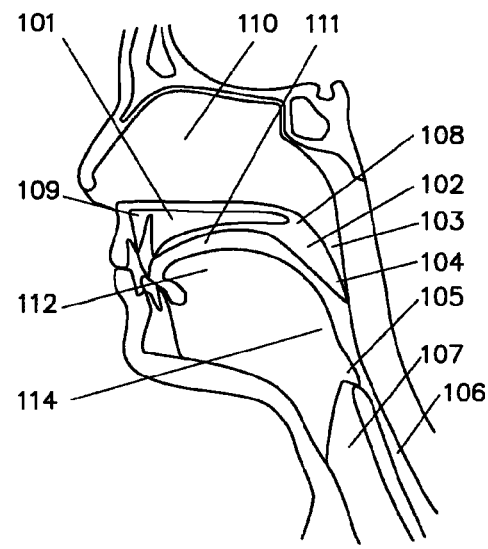
FIG. 2 is a cross-sectional side view of a human head during swallowing.

FIG. 2 is a cross-sectional side view of a human head during swallowing. When a human is swallowing, the soft palate 102 moves backwards, and nasopharynx 103 is blocked. At the same time, the epiglottis 105 blocks the trachea 107, and food enters esophagus 106 via pharynx.

Figure 3:
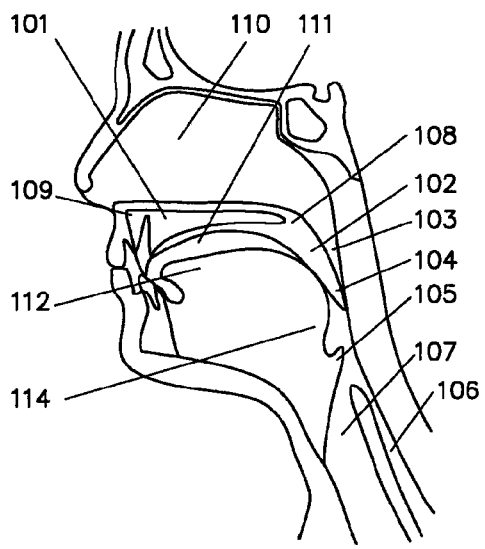
FIG. 3 is a view depicting occurrence of OSAHS in a patient.
Figure 4:
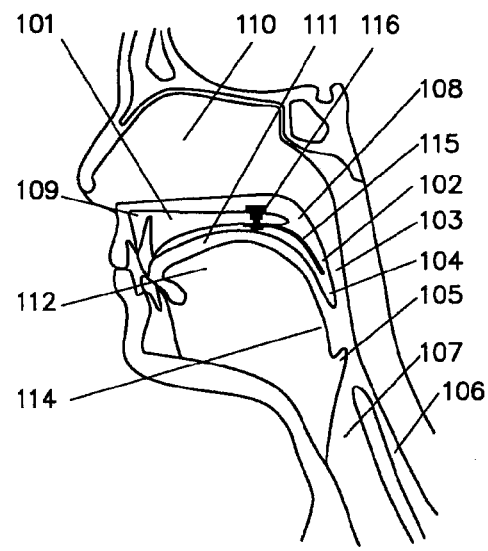
FIG. 4 is a view depicting the principle of a method for treating OSAHS according to the present invention and the working principle of an implanted soft palate support of the present invention.
Figure 5:
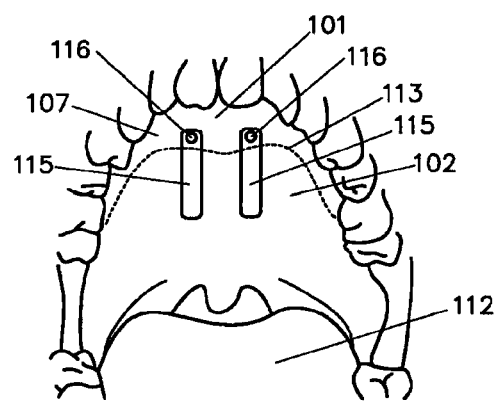
FIG. 5 is a schematic structural view of implanting an implanted soft palate support of the present invention into a hard palate and a soft palate.
Figure 6:
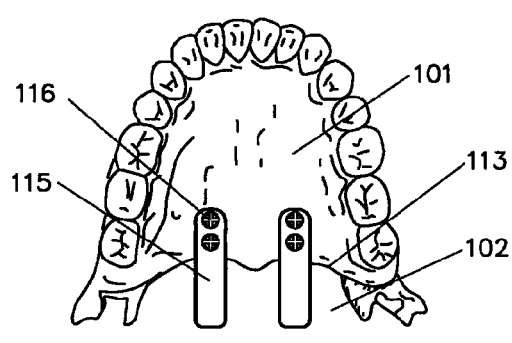
FIG. 6 is a schematic view of a method for fixing two implanted soft palate supports of the present invention to a hard palate.
Figure 7:
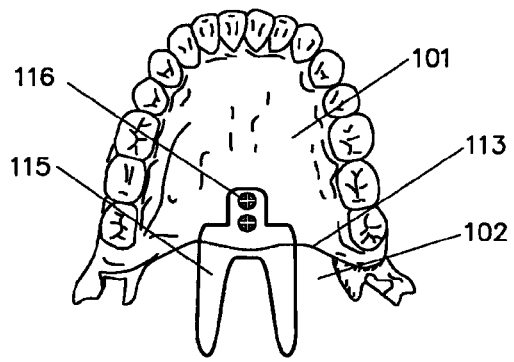
FIG. 7 is a schematic view of a method for fixing one implanted soft palate support of the present invention to a hard palate.

FIG. 3 is a view depicting occurrence of OSAHS in a patient. When OSAHS occurs in a patient, soft tissues of the upper airway collapse, and the upper airway is obstructed, resulting in insufficient airflow and even apnea. Specifically, when OSAHS occurs, the soft palate 102 of the patient collapses backwards, so that the passage between soft palate 102 and nasopharynx 103 becomes narrow or is blocked, and at the same time soft tissues of the tongue root collapse, and thus, the passage between tongue root 114 and soft palate 102 becomes narrow or is blocked, resulting in insufficient airflow during breathing and even apnea. For some OSAHS patients, the collapse of the soft palate 102 not only directly causes the passage between soft palate 102 and nasopharynx 103 narrow or blocked, but also directly causes the passage between tongue root 114 and soft palate 102 narrow or blocked, resulting in insufficient airflow during breathing or apnea.

In the present invention, the soft palate 102 is lifted or the tongue root 114 is indirectly lifted by implanting a soft palate support into the hard palate 101 and the soft palate 102, so as to enlarge the passage between soft palate 102 and nasopharynx 103, thereby achieving the objective of treating OSAHS. Specifically, the implanted soft palate support includes a hard palate connecting end 1 and a support 2. The hard palate connecting end 1 has a connecting structure 11 configured to be connected with a hard palate, and the connecting structure 11 is connected and firmly fixed to a back end of the hard palate 101 via a fastener 116. The support 2 is a flat implant with a certain supporting force, and the support 2 is inserted into the soft palate to raise or lift the soft palate, so as to enlarge the passage between soft palate 102 and nasopharynx 103, thereby achieving the objective of treating OSAHS. See FIG. 4 to FIG. 7 and FIG. 34 to FIG. 35. The support 2 has a thickness of 0.01-5 mm, and most preferably 0.2-1.1 mm.

It should be particularly noted that, one end (the hard palate connecting end 1) of the implanted soft palate support of the present invention is fixed to the hard palate, and the other end (the support 2) is implanted into a muscular layer of the soft palate. The support 2 implanted into the muscular layer of the soft palate is a flat implant, which not only provides for the convenience of inserting or implanting the support 2 into the muscular layer of the soft palate, but more importantly can effectively lift the soft palate, bear and separate the force generated when the soft palate swings. A cutting force generated when the soft palate swings back and forth after the support 2 is implanted into the soft palate is reduced by increasing the contact area of the support 2. Therefore, the cutting force of a non-flat implant (such as a single fine metal wire) generated when the soft palate swings back and forth is avoided. After the support is implanted for a long time, the cutting force generated when the soft palate swings back and forth will cause the non-flat implant (such as a single fine metal wire) to shift in the soft palate, or even to be exposed. When the non-flat implant shifts in the soft palate or is even exposed, the patient will have a strong foreign body sensation, and the support fails to lift the soft palate at the same time. Therefore, it is necessary to use a flat implant as the support 2, so as to effectively prevent the support 2 from shifting after being implanted into the soft palate, and effectively lift the soft palate.

The method and implanted instrument of the present invention for treating OSAHS have the advantages of small wound, fast recovery, and significant effect, thereby realizing an objective of minimally invasive treatment. Since one end (the hard palate connecting end 1) of the implanted soft palate support of the present invention is firmly fixed to the hard palate and may act as a force-bearing fulcrum, and the other end, that is, the support 2 is implanted into the soft palate, the lifting degree of the soft palate being supported may further be adjusted within a certain range by adjusting the shape and degree of curvature of the support 2, so as to achieve an optimal treatment effect.

In particular, for the patient implanted with the implanted soft palate support of the present invention, after surgery, when the patient is induced to sleep, the lifting degree of the soft palate being supported may be adjusted within a certain range by adjusting the shape and degree of curvature of the support 2 under the monitor of an electronic laryngoscope, so as to achieve optimal treatment effect and comfort. Clinical application has proved that, the treatment method and the implanted instrument are popular with patients for treating OSAHS and snoring because of small wound, reliable efficacy, and great comfort.

Embodiment 1

An Implanted Soft Palate Support of the Present Invention when the Connecting Structure of the Hard Palate Connecting End is a Hole Structure The product of the present invention is produced and manufactured by selecting a medical grade titanium metal plate capable of being implanted into a human body for a long term according to a common process procedure of titanium metal products, and then, the implanted soft palate support of the present invention may be obtained. See FIG. 8 to FIG. 13. The hard palate connecting end 1 of the implanted soft palate support of the present invention may be firmly fixed to the hard palate 101 by adopting the through hole-shaped connecting structure 11 via the fastener 116 (such as a titanium bone nail, a titanium rivet, a titanium nut bolt structure, a titanium metal male and female engagement fastening structure, and various other fasteners). The number of through holes on the hard palate connecting end 1 for positioning may be multiple, for example, two, three, or four. In principle, each implanted soft palate support of the present invention may be firmly fixed by using one through hole or two through holes at most.

Figure 8:
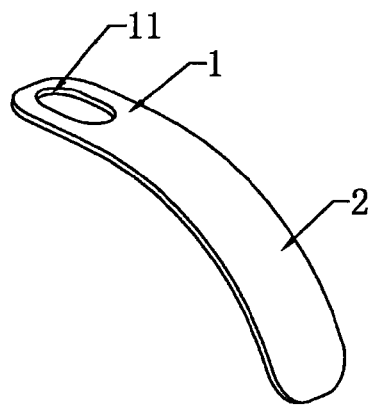
FIG. 8 is a schematic structural view of an implanted soft palate support of the present invention wherein the connecting structure of the hard palate connecting end is a hole structure.
Figure 9:
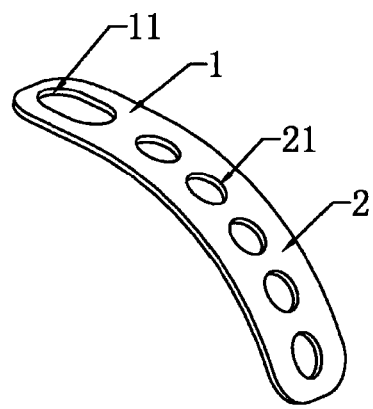
FIG. 9 is a schematic structural view of an implanted soft palate support of the present invention wherein the support includes through holes.

As shown in FIG. 8 and FIG. 9, the connecting structure of the hard palate connecting end is a rectangular through hole structure, so that the hard palate connecting end of the implanted soft palate support of the present invention is conveniently fixed to the hard palate via the fastener (such as a titanium bone nail, a titanium rivet, a titanium nut bolt structure, a titanium metal male and female engagement fastening structure, and various other fasteners), and the length and degree of curvature of the soft palate support inserted into the soft palate may be adjusted within a certain range, so as to control and adjust the lifting degree of the soft palate.

Referring to FIG. 9, the support of this embodiment has one or more through holes, so as to enhance the degree of bonding between the support and the soft palate tissues. The soft palate tissues may penetrate through the through holes configured on the support, which increases the bonding force between the soft palate tissues and the support.

Figure 10:
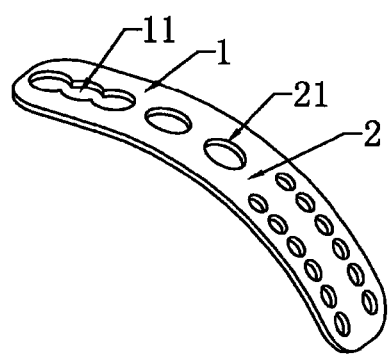
FIG. 10 is a schematic structural view of an implanted soft palate support of the present invention wherein the connecting structure of the hard palate connecting end is a waist drum-shaped hole structure.

As shown in FIG. 10, the connecting structure of the hard palate connecting end is designed to be a waist drum-shaped through hole structure, so that the position where the hard palate connecting end of the implanted soft palate support of the present invention is fixed to the hard palate may be conveniently adjusted, so as to adjust the length and degree of curvature of the support inserted into the soft palate, thereby controlling and adjusting the lifting degree of the soft palate.

In addition, the layout and size of the through holes configured on the support are also different from those in FIG. 9.

Figure 11:
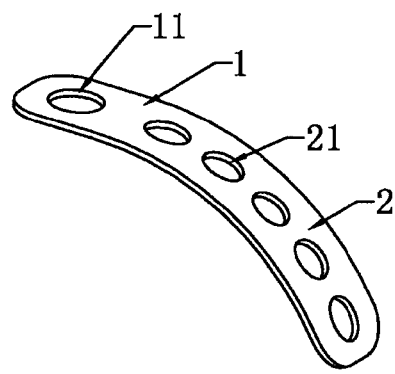
FIG. 11 is a schematic structural view of an implanted soft palate support of the present invention wherein the connecting structure of the hard palate connecting end is a circular through hole structure.

As shown in FIG. 11, the connecting structure of the hard palate connecting end directly adopts the simplest circular through hole structure.

Figure 12:
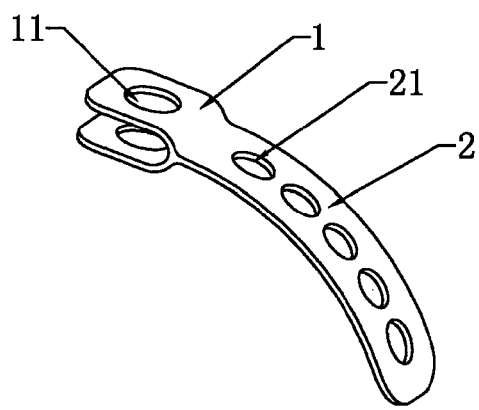
FIG. 12 is a schematic structural view of an implanted soft palate support of the present invention wherein the connecting structure of the hard palate connecting end is a U-shaped clamp structure.

As shown in FIG. 12, the hard palate connecting end is designed with a U-shaped clamp structure, the U-shaped clamp clamps onto the hard palate, and a fastener may be further used for reinforcement. The degree of curvature of the support may be adjusted by bending the support to enable the support to plastically deform, so as to control and adjust the lifting degree of the soft palate.

Figure 13:
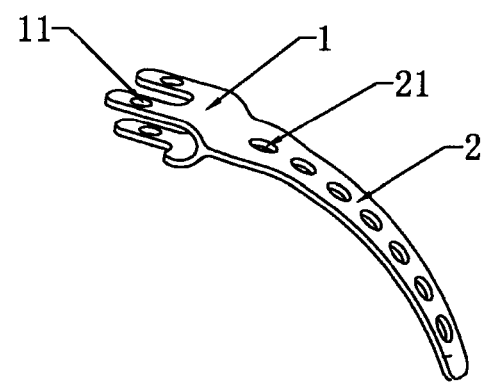
FIG. 13 is a schematic structural view of an implanted soft palate support of the present invention wherein the connecting structure of the hard palate connecting end is an epsilon-type U-shaped clamp structure.

As shown in FIG. 13, the hard palate connecting end is designed with an epsilon-type U-shaped clamp structure, the epsilon-type U-shaped clamp clamps onto the hard palate, and a fastener may be further used for reinforcement. The degree of curvature of the support may be adjusted by bending the support to enable the support to plastically deform, so as to control and adjust the lifting degree of the soft palate.

In a clinical surgery, in order to adjust the lifting degree of the soft palate, the following methods may be adopted. First, the fixed position of the hard palate connecting end 1 is adjusted. Second, the degree of curvature of the support 2 is adjusted. Third, the length of the support 2 inserted into the soft palate 102 is adjusted. All the three methods can effectively adjust the lifting degree of the soft palate, so as to achieve an optimal treatment effect. The connecting structure 11 of the hard palate connecting end in FIG. 8 is a rectangular through hole structure, and the connecting structure 11 of the hard palate connecting end in FIG. 10 is a waist drum-shaped through hole, both for the convenience of adjusting the position where the hard palate connecting end 1 of the implanted soft palate support of the present invention is fixed to the hard palate 101, so as to adjust the length and degree of curvature of the support 2 inserted into the soft palate 102, thereby controlling and adjusting the lifting degree of the soft palate. Many specific products may be further designed according to the technical solution of the present invention.

What is of particular interest is that, after surgery, when the patient is induced to sleep, the lifting degree of the soft palate being supported may be adjusted within a certain range by adjusting the shape and degree of curvature of the implanted soft palate support under the monitor of an electronic laryngoscope, so as to achieve an optimal treatment effect. Clinical application has proved that, the treatment method and the implanted instrument are popular with patients for treating OSAHS and snoring because of small wound, reliable efficacy, little foreign body sensation, and great comfort.

The implanted soft palate support of the present invention may be made of any material capable of being implanted into a pharynx for a long term and having a certain force bearing function. Medical titanium metal and titanium alloys are preferred materials. Among the titanium alloys, a titanium-nickel shape memory alloy (such as the Nitinol alloy) and a titanium-zirconium-niobium alloy are particularly suitable for manufacturing a tail portion of the support 2 because of superelasticity and shape memory capability thereof, so as to meet the requirement that the tail portion of the support 2 needs to swing along with the soft palate 102; and may be designed into a fixed connecting structure 11 with a self-locking function because of shape memory characteristics thereof. As shown in FIG. 24 and FIG. 25, the hard palate connecting end is firstly manufactured by using a medical titanium alloy; then, the tail portion of the support is manufactured by using a titanium-nickel shape memory alloy wire and is then thermally set into a shape with a radian matching the curvature of the soft palate of the human body when it relaxes; and finally, a head end of the memory alloy wire is riveted to the hard palate connecting end made of the titanium alloy, thereby obtaining the implanted soft palate support of the present invention having a strong supporting force, good flexibility and good elasticity.

Figure 14:
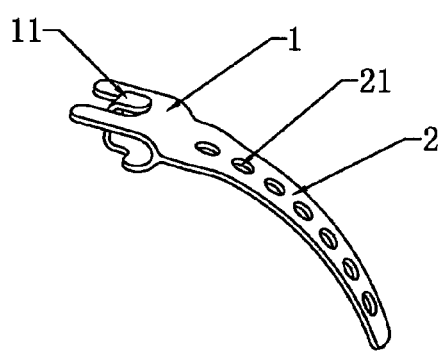
FIG. 14 is a schematic structural view of an implanted soft palate support of the present invention wherein the connecting structure of the hard palate connecting end is a lock cache structure.
Figure 15:
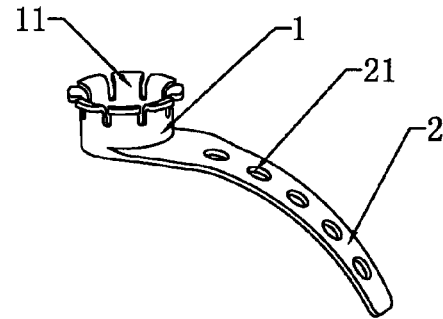
FIG. 15 is a schematic structural view of an implanted soft palate support of the present invention wherein the connecting structure of the hard palate connecting end is a rivet-type structure.
Figure 16:
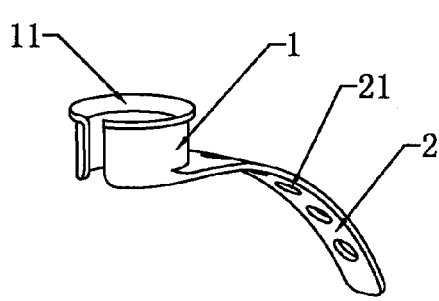
FIG. 16 is a schematic structural view of an implanted soft palate support of the present invention wherein the connecting structure of the hard palate connecting end is a self-expanding lock structure.

In the embodiments shown in FIG. 14 to FIG. 16, the hard palate connecting end 1 may be made of a titanium-nickel shape memory alloy. In use, the connecting structure 11 of the hard palate connecting end 1 contracts in cold water (0° C.-15° C.), and after being passed through the through hole bored into the hard palate, the connecting structure 11 of the hard palate connecting end recovers to the geometrical shape set during the thermal setting process under the effect of body temperature, so that the implanted soft palate support of the present invention is firmly fixed to the hard palate.

As shown in FIG. 14, the hard palate connecting end is designed with a lock cache structure. In use, a through hole is firstly bored into the hard palate, and a hook is passed through the through hole bored into the hard palate, and then hooked to the hard palate, thereby forming a fixed structure. The degree of curvature of the support may be adjusted by bending the support to enable the support to plastically deform, so as to control and adjust the lifting degree of the soft palate. This embodiment may be made of titanium metal, and more particularly may be made of a titanium-nickel shape memory alloy (Nitinol alloy). A required geometrical shape of a product above a recovery temperature is set according to shape memory characteristics of a shape memory alloy (usually a memory alloy with a recovery temperature between 20° C. and 33° C.). In use, the connecting structure of the hard palate connecting end contracts in cold water (0° C.-15° C.), and after being passed through the through hole bored into the hard palate, the connecting structure of the hard palate connecting end recovers to the geometrical shape set during the thermal setting process under the effect of body temperature, so that the implanted soft palate support of the present invention is firmly fixed to the hard palate.

As shown in FIG. 15, the hard palate connecting end is designed with a rivet-type structure. In use, a through hole is firstly bored into the hard palate, a rivet is passed through the through hole bored into the hard palate, and then the hard palate connecting end is riveted to the hard palate with a special surgical instrument, thereby forming a fixed structure. The degree of curvature of the support may be adjusted by bending the support to enable the support to plastically deform, so as to control and adjust the lifting degree of the soft palate.

As shown in FIG. 16, the hard palate connecting end is designed with a self-expanding lock structure. In use, a through hole is firstly bored into the hard palate, and then the self-expanding lock structure is passed through the through hole bored into the hard palate, and thus the hard palate connecting end is fixed to the hard palate under an elastic restoring force. The degree of curvature of the support may be adjusted by bending the support to enable the support to plastically deform, so as to control and adjust the lifting degree of the soft palate. Similar to the embodiment in FIG. 15, the embodiment in FIG. 16 may also be made of a titanium-nickel shape memory alloy for the convenience of implantation.

The support 2 of the implanted soft palate support of the present invention has one or more through holes 21 or convex-concave lines 22, which may enhance the adhesion between the support 2 and soft palate tissues. The through holes 21 may be arranged in many different manners, and the convex-concave lines 22 may also be designed in many ways, and FIG. 17 and FIG. 18 show two different specific design solutions.

Figure 17:
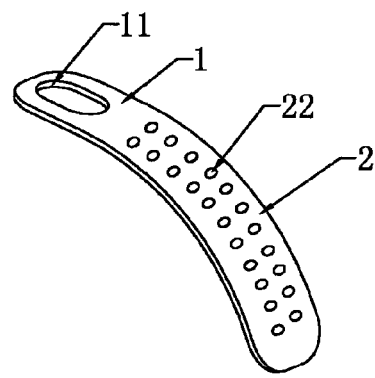
FIG. 17 is a schematic structural view of an implanted soft palate support of the present invention wherein the support includes convex-concave lines.
Figure 18:
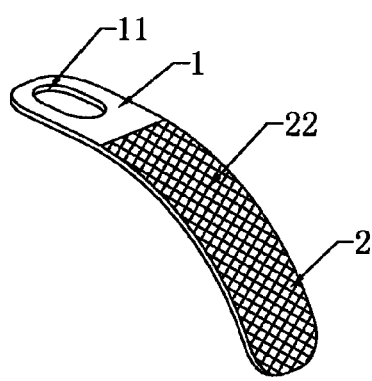
FIG. 18 is a schematic structural view of an implanted soft palate support of the present invention wherein the support includes knurled convex-concave lines.
Figure 28:
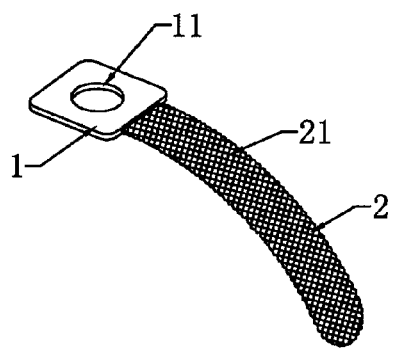
FIG. 28 is a schematic structural view of an implanted soft palate support of the present invention wherein the support is a wire mesh structure.
Figure 29:
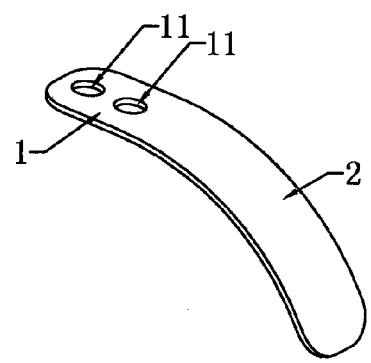
FIG. 29 is a schematic structural view of an implanted soft palate support of the present invention wherein the connecting structure of the hard palate connecting end is a double-hole structure, which is firmly fixed to a hard palate.

As shown in FIG. 17, convex-concave lines are used to enhance the bonding force between the support and the soft palate. As shown in FIG. 28, knurled convex-concave lines are used to enhance the bonding force between the support and the soft palate. In FIG. 25, the support is a meshwork (such as a meshwork braided by titanium alloy wires and a meshwork braided by Nitinol alloy wires) braided by metal wires, one end of the wire mesh is connected to the hard palate connecting end, and the other end may be inserted into the soft palate.

Figure 19:
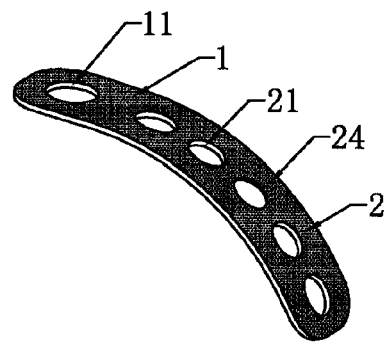
FIG. 19 is a schematic structural view of an implanted soft palate support of the present invention wherein the support includes a biocompatible coating.
Figure 26:
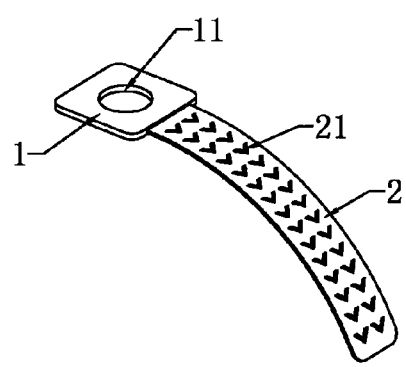
FIG. 26 is a schematic structural view of an implanted soft palate support of the present invention wherein the support includes V-shaped through holes, which enhances the bonding force between the support and a soft palate.
Figure 27:
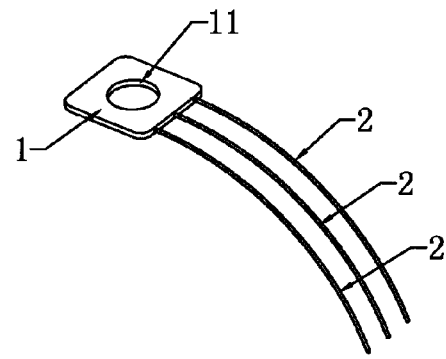
FIG. 27 is a schematic structural view of an implanted soft palate support of the present invention wherein the support is a simple structure including three parallel alloy wires (such as titanium alloy wires or Nitinol alloy wires), and the alloy wires are connected to the hard palate connecting end.

In order to improve the biocompatibility of the implanted soft palate support of the present invention with human tissues, surface treatment may also be performed on the implanted soft palate support to configure a biocompatible coating 24, so as to improve the biocompatibility of the support and enhance the bonding force between the support and the soft palate. See FIG. 19. One of the adopted methods is to spray various coatings, in which a biodegradable material may be coated, such as polylactic acid, polylactic acid-polyether copolymer, polycaprolactone, polycaprolactone-polyether block copolymer, polycaprolactone copolymer, polycaprolactone-polyether-polylactide copolymer, poly(glycolide-polylactide)copolymer, glycolide-L-lactide-caprolactone copolymer, polycaprolactone-polylactide-polyglycolide copolymer, and other fatty acid polylactone copolymer, and collagen, chitosan, gelatin, alginate natural polymer material, or a blend thereof; or a non-absorbable material may be coated, such as hydroxyapatite and various biological ceramics. In addition, it is also one of the effective methods to perform surface treatment for titanium and the titanium alloy, for example, plasma spraying is performed for titanium and the titanium alloy, a porous structure is manufactured on the surface, or a coating is manufactured by a magnetron sputtering method.

Embodiment 2

An Implanted Soft Palate Support of the Present Invention when the Connecting Structure of the Hard Palate Connecting End is a Lock Cache Structure In this embodiment, the connecting structure 11 of the hard palate connecting end is a lock cache structure. The hard palate connecting end 1 is designed with a lock cache structure. In use, a through hole is firstly bored into the hard palate 101, and a lock cache 11 is passed through the through hole bored into the hard palate, and then locked to the hard palate 101, thereby forming a fixed structure. The degree of curvature of the support 2 may be adjusted by bending the support 2 to enable the support 2 to plastically deform, so as to control and adjust the lifting degree of the soft palate 102. This embodiment may be made of titanium metal, and more particularly may be made of a titanium-nickel shape memory alloy (Nitinol alloy). A required geometrical shape of a product above a recovery temperature is set according to shape memory characteristics of a shape memory alloy (usually a memory alloy with a recovery temperature between 20° C. and 33° C.). In use, the connecting structure 11 of the hard palate connecting end contracts in cold water (0° C.-15° C.), and after being passed through the through hole bored into the hard palate, the connecting structure 11 of the hard palate connecting end recovers to the geometrical shape set during the thermal setting process under the effect of body temperature, so that the implanted soft palate support of the present invention is firmly fixed to the hard palate. See FIG. 14 and FIG. 16.

Embodiment 3

A Combined-Type Implanted Soft Palate Support of the Present Invention

Figure 33:
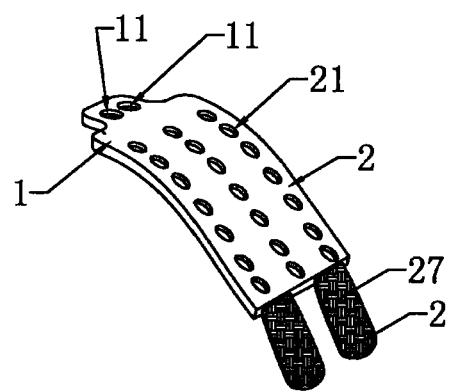
FIG. 33 is a schematic structural view of an implanted soft palate support of the present invention in the form of an integral stamped plate with tail fins.
Figure 34:
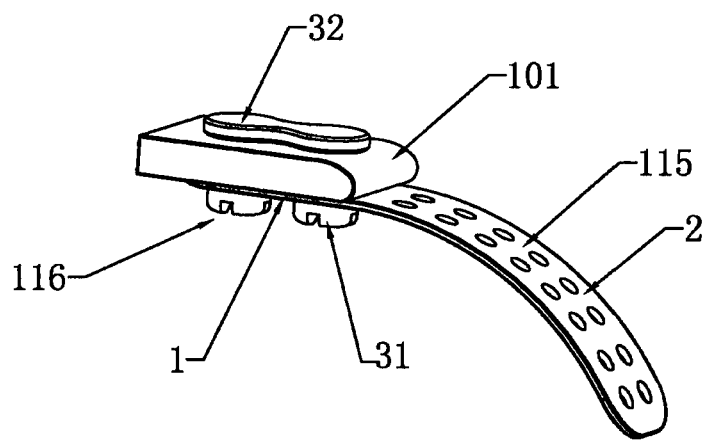
FIG. 34 is a schematic structural view of an implanted soft palate support of the present invention when it is fixed to a hard palate.
Figure 35:
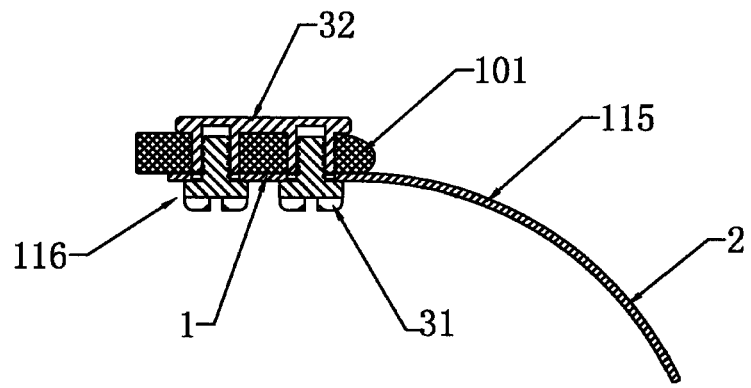
FIG. 35 is a cross-sectional view of FIG. 34 depicting the structure when the implanted soft palate support of the present invention is fixed to the hard palate.

In this embodiment, the hard palate connecting end 1 and the support 2 form a combined-type structure. See FIG. 24 and FIG. 33.

As shown in FIG. 24, firstly, the hard palate connecting end 1 and a part of the support 2 are manufactured by using a medical titanium alloy; then, a memory alloy wire braid is formed by braiding a titanium-nickel shape memory alloy wire and is thermally set to serve as a tail portion of the support 2; and finally, a head end of the memory alloy wire braid is riveted to the hard palate connecting end 1 made of the titanium alloy or to a front portion of the support 2. The product of this embodiment ensures the supporting and lifting forces of the soft palate, and the wire braid at the tail portion of the support 2 has good flexibility and elasticity, so as to meet the requirement that the tail portion of the support 2 needs to swing back and forth along with a tail end 104 of the soft palate 102. In addition, the braid at the tail portion may also be made of a medical polymer material thread (such as polyester thread and polyurethane thread).

Figure 32:
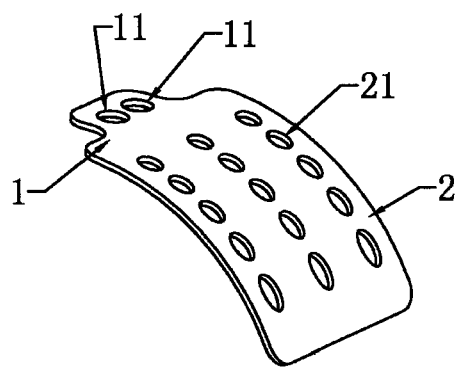
FIG. 32 is a schematic structural view of an implanted soft palate support of the present invention in the form of an integral stamped plate.

The embodiment shown in FIG. 32 is manufactured by adopting an integral stamping manufacturing process. The connecting structure of the hard palate connecting end is a double-pore structure, which may be firmly fixed to the hard palate, and a stamped plate is used as the support and may be inserted into the soft palate. The difference between FIG. 33 and FIG. 32 lies in that, in FIG. 33, tail fins made of the braid is embedded in the tail portion of the support, and the tail fins which are soft and elastic may swing along with the tail end of the soft palate, and have good flexibility.

In this embodiment, the soft and elastic tail fins of the support 2 that may swing back and forth along with the tail end 104 of the soft palate may be manufactured in various manners, and is preferably manufactured by using a complex braid of a spring wire of a Nitinol alloy or titanium-zirconium-niobium superelastic alloy.

Embodiment 4

An Implanted Soft Palate Support of the Present Invention with a Blunt Edge In order to increase the contact area of an edge of the implanted soft palate support of the present invention, and achieve an objective of blunting the edge; the edge of the support 2 may be wrapped with a thread (such as a titanium-nickel shape memory alloy wire, a polyester thread, a polyurethane thread, and other polymer material threads). As such, not only the edge effect of the support 2 is improved, the contact area of the edge is increased, and the objective of blunting the edge is achieved, but also the degree of curvature of the support 2 may be adjusted, and the support 2 has good flexibility. See FIG. 20 to FIG. 23.

As shown in FIG. 20 and FIG. 21, the edge of the support is blunted. By wrapping the edge, the edge effect of the support is improved, the contact area of the edge is increased, and the objective of blunting the edge is achieved, and further, the rigidity of the support may be enhanced.

As shown in FIG. 22, the edge of the support 2 is blunted with a medical polymer material thread 28. Holes or grooves 29 are firstly cut on the edge of the support before blunting, and then the edge of the support 2 is wrapped with a medical polymer material thread 28 to form a blunt edge 23, so as to improve the edge effect of the support, increase the contact area of the edge, and achieve the objective of blunting the edge.

As shown in FIG. 23, a chip of the support is wrapped with a titanium-nickel shape memory alloy wire. As such, not only the edge effect of the support is improved, the contact area of the edge is increased, and the objective of blunting the edge is achieved, but also the degree of curvature of the support may be adjusted, and the support has good flexibility.

Embodiment 5

An Implanted Soft Palate Support of the Present Invention with a Biocompatible Coating In this embodiment (see FIG. 19), a biocompatible coating 24 is configured on the support 2, so as to enhance the bonding force between the support and the soft palate.

In order to improve the biocompatibility of the implanted soft palate support of the present invention with human tissues, surface treatment may be performed on the implanted soft palate support to manufacture a coating 24 capable of improving biocompatibility. One of the adopted methods is to spray various coatings, in which a biodegradable material may be coated, such as polylactic acid, polylactic acid-polyether copolymer, polycaprolactone, polycaprolactone-polyether block copolymer, polycaprolactone copolymer, polycaprolactone-polyether-polylactide copolymer, poly(glycolide-polylactide)copolymer, glycolide-L-lactide-caprolactone copolymer, polycaprolactone-polylactide-polyglycolide copolymer, and other fatty acid polylactone copolymer, and collagen, chitosan, gelatin, alginate natural polymer material, or a blend thereof; or a non-absorbable material may be coated, such as hydroxyapatite and various biological ceramics. In addition, it is also one of the effective methods to perform surface treatment for titanium and the titanium alloy, for example, plasma spraying is performed for titanium and the titanium alloy, a porous structure is manufactured on the surface, or a coating is manufactured by a magnetron sputtering method.

Embodiment 6

A Fork-Shaped Implanted Soft Palate Support of the Present Invention

Figure 30:
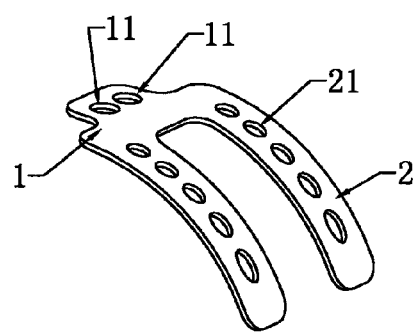
FIG. 30 is a schematic structural view of an implanted soft palate support of the present invention having a shape of a fork and two through-holes near the hard palate connecting end.
Figure 31:
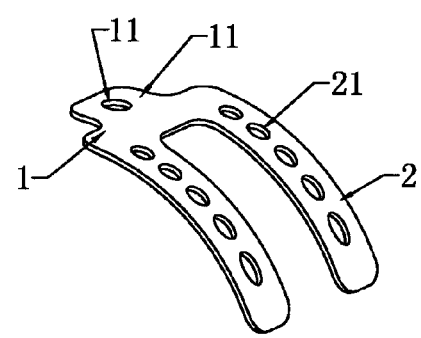
FIG. 31 is a schematic structural view of an implanted soft palate support of the present invention having a shape of a two-prong fork and one through-hole near the hard palate connecting end.

In this embodiment, the implanted soft palate support is in a shape of a fork. The connecting structure 11 of the hard palate connecting end 1 is a double though hole structure, which may be firmly fixed to the hard palate 101 via the fastener 116, and two prongs of the fork are used as the support 2 and may be inserted into the soft palate 102. See FIG. 30 to FIG. 31. FIG. 31 is the same as FIG. 30, except that in FIG. 31, the connecting structure of the hard palate connecting end is a single hole structure.

Embodiment 7

An Implantation Method of the Implanted Soft Palate Support of the Present Invention The implantation method of the present invention is: through a surgery, the support 2 of the implanted soft palate support 115 of the present invention is firstly inserted into the soft palate 102 by a length equal to 1/5 to 4/5, and most preferably, 2/3 to 3/4, of a total length of the soft palate 102. Then, holes are bored on the hard plate 101, and the hard palate connecting end 1 of the implanted soft palate support 115 of the present invention is fixed to the hard palate 101 close to the hard palate-soft palate junction 113 via the fastener 116. See FIG. 34 and FIG. 35. The degree of curvature of the support 2 may be adjusted by bending the support 2 to enable the support 2 to plastically deform, so as to control and adjust the lifting degree of the soft palate 102, thereby achieving an optimal treatment effect. The tissues are sutured, thus completing the implantation surgery.

The fastener 116 may be a fastener of a nut bolt structure, which is particularly suitable for fixing the implanted soft palate support 115 of the present invention to plate-like bone tissues such as the hard palate 101. The screw thread of the fastener 116 is between metal pieces or plastic pieces, which overcomes the defect that an ordinary titanium bone nail cannot be easily fixed to the hard palate 101 with a screw because the hard palate 101 is too thin.

In particular, for the patient implanted with the implanted soft palate support of the present invention, after surgery, when the patient is induced to sleep, the lifting degree of the soft palate 102 being supported may be adjusted within a certain range by adjusting the shape and degree of curvature of the implanted soft palate support 115 under the monitor of an electronic laryngoscope, so as to achieve optimal treatment effect and comfort. Clinical application has proved that, the treatment method and the implanted instrument are popular with patients for treating OSAHS and snoring because of small wound and reliable efficacy.

Embodiment 8

An Implanted Soft Palate Support of the Present Invention Including an Elastic Module Made of a Flexible Polymer Material A blank of the product of the present invention is produced and manufactured by selecting a medical grade titanium metal plate capable of being implanted into a human body for a long term according to a common process procedure of titanium metal products. Many small through holes, which are used for penetration and shaping of medical silica gel, are opened at a distal end (also referred to as the tail) of the support 2 and on the titanium plate which is used to manufacture the rigid module 40. A formed silica gel transition layer is an elastic module 20. The distal end of the support 2 and the rigid module 40 are connected together by the elastic module 20 made of silica gel. Thus, the implanted soft palate support of the present invention with an elastic module made of a flexible polymer material is obtained. See FIG. 36, FIG. 36-1, and FIG. 36-2.

Figure 36:
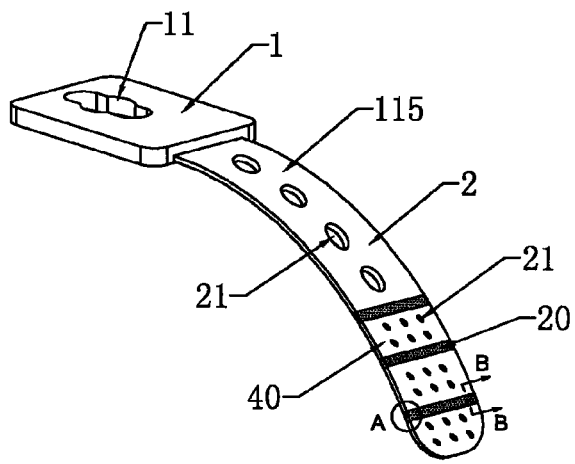
FIG. 36 is a schematic structural view of an implanted soft palate support including a rigid module and an elastic module made of a flexible polymer material according to the present invention, wherein the degree of curvature of the support may be adjusted by bending the rigid module of the support and causing plastic deformation to the rigid module under an external force, so as to control and adjust the lifting degree of a soft palate; and the elastic module enables the support to maintain good flexibility, such that it can not only move with the swinging of the soft palate, but also help the soft palate restore to a relaxed state; in other words, a restoring force of the elastic module after the plastic deformation helps the soft palate restore to the relaxed state, thereby raising or pulling up the soft palate.
Figures 1, 36:
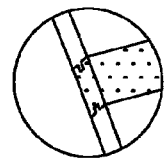
Figures 2, 36:
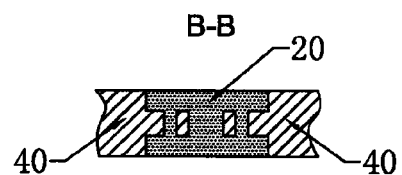
Figure 37:
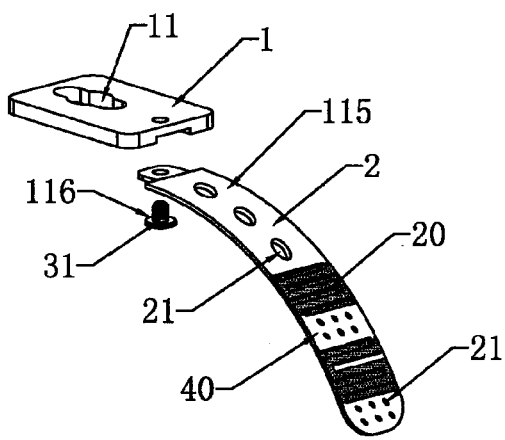
FIG. 37 is a schematic structural view of a combined-type implanted soft palate support of the present invention before being assembled.
Figure 38:
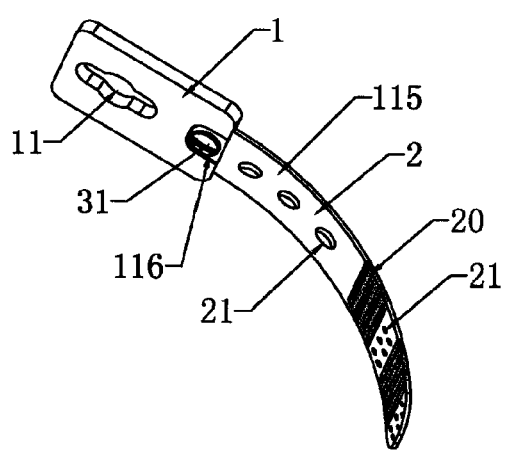
FIG. 38 is a schematic structural view of FIG. 37 after being assembled.

As shown in FIG. 36, the elastic module and the rigid module are alternately mounted on the tail portion of the support, so as to provide the tail portion of the support with good flexibility and an excellent restoring force after tensile deformation. The elastic module is made of a flexible polymer material, and the soft palate tissues cannot easily penetrate the elastic module. The elastic module may move within a certain range, and may generate an excellent restoring force. The rigid module is made of a light porous material (such as porous polythene, porous polypropylene, and a titanium metal plate with through holes), so that the soft palate tissues may penetrate and grow on the rigid module, thereby increasing the bonding force between the soft palate tissues and the support. As such, under an external force generated during breathing, the elastic module of the support may generate an excellent restoring force to lift the soft palate tissues growing on and attached to the rigid module, so as to help the soft palate restore to a normal position when the soft palate relaxes, thereby preventing OSAHS and snoring from occurring.

The flexible polymer materials for manufacturing the elastic module 20 include, but are not limited to, medical silica gel, medical polyurethane, and other elastic polymer materials capable of being implanted into the human body for a long term.

The materials for manufacturing the rigid module 40 include, but are not limited to, titanium metal, a titanium alloy, a Nitinol alloy, a medical polymer material (such as porous polythene, porous polypropylene, and porous polytetrafluoroethylene), and other materials capable of being implanted into the human body for a long term.

The materials for manufacturing the support 2 include, but are not limited to, titanium metal, a titanium alloy, a titanium-zirconium-niobium alloy, a Nitinol alloy, a medical polymer material, and other materials capable of being implanted into the human body for a long term.

The materials for manufacturing the hard palate connecting end 1 include, but are not limited to, titanium metal, a titanium alloy, a Nitinol alloy, a medical polymer material, and other materials capable of being implanted into the human body for a long term.

The materials for manufacturing the fastener 116 include, but are not limited to, titanium metal, a titanium alloy, a Nitinol alloy, a medical polymer material, and other materials capable of being implanted into the human body for a long term.

The feature of this embodiment lies in that, the distal end (also referred to as the tail portion) of the support 2 at least includes one elastic module 20. The elastic module 20 has good elasticity, while the rigid module 40 is not readily deformable, but has a rough surface or holes, which facilitates tissue penetration and growth. In the implanted soft palate support of the present invention, the near end of the support 2 has a good lifting force for the soft palate 102, and the tail portion has excellent flexibility and restoring force due to the configuration of the elastic module, which not only maintains the flexibility of the tail of the soft palate 102, but also enhances the lifting force of the soft palate for restoring to the relaxed state of the soft palate during breathing, thereby producing a better treatment effect. See FIG. 36 and FIG. 49 to FIG. 54.

Embodiment 9

An Implanted Soft Palate Support of the Present Invention with an Elastic Module of a Spring Structure The difference between this embodiment and the eighth embodiment lies in that, in this embodiment, the elastic module 20 directly adopts a spring structure.

Figure 57:
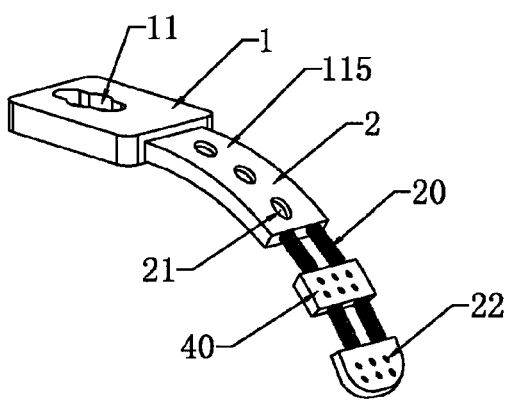
FIG. 57 is a schematic structural view of an implanted soft palate support of the present invention wherein a coil spring is adopted as an elastic module.
Figure 58:
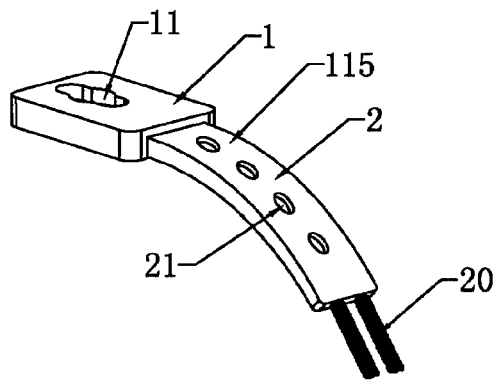
FIG. 58 is a schematic structural view of an implanted soft palate support of the present invention wherein a coil spring, which is adopted as an elastic module, may be wrapped or wound by soft palate tissues, thereby enhancing a lifting force of the soft palate for restoring to the relaxed state of the soft palate during breathing.

For example, a coil spring made of an elastic alloy wire may be directly used to manufacture the elastic module 20 (see FIG. 57 and FIG. 58). During the manufacturing process, the coil spring is connected to the tail portion of the support 2, or between the tail portion of the support 2 and the rigid module 40, or between the rigid modules 40. Such a spring structure has good flexibility and restoring force, which not only maintains the flexibility of the tail of the soft palate 102, but also enhances the lifting force of the soft palate for restoring to the relaxed state of the soft palate during breathing.

Figure 59:
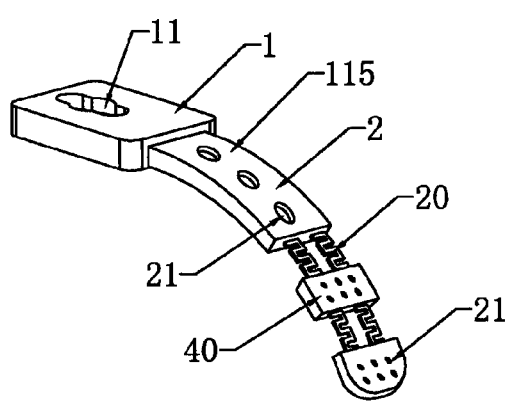
FIG. 59 is a schematic structural view of an implanted soft palate support of the present invention wherein a spring formed by laser engraving is adopted as an elastic module.
Figure 60:
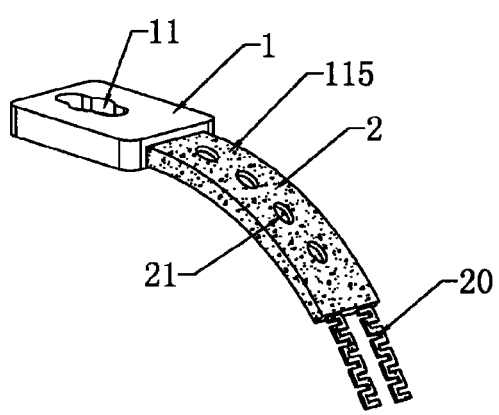
FIG. 60 is a schematic structural view of an implanted soft palate support of the present invention wherein a spring formed by laser engraving, which is adopted as an elastic module, may be wrapped or wound by soft palate tissues, thereby enhancing a lifting force of the soft palate for restoring to the relaxed state of the soft palate during breathing; and the spring formed by laser engraving in this embodiment may not be coated with a flexible polymer material, but has a coating capable of improving biocompatibility.

A spring structure may be formed on the tail portion of the support 2 by a laser engraving method to serve as the elastic module 20 (see FIG. 59 and FIG. 60). The spring structure may have different engraved patterns. The elastic module 20 formed by the spring structure is wrapped and wound by the soft palate tissues, thereby enhancing the lifting force of the soft palate for restoring to the relaxed state of the soft palate during breathing. In the implanted soft palate support of the present invention with this structure, the near end of the support 2 has a good lifting force for the soft palate 102, and the tail portion has excellent flexibility and restoring force as the spring structure is wrapped and wound by the soft palate tissues, which not only maintains the flexibility of the tail of the soft palate 102, but also enhances the lifting force of the soft palate for restoring to the relaxed state of the soft palate during breathing. Therefore, the structure is simpler, and the connection is firm.

In addition, when the support 2 is made of the Nitinol alloy, a part of the support 2 close to the hard palate connecting end 1 may be annealed by local heat treatment and thus become plastically deformable under an external force, with other parts still maintaining superelasticity and shape memory capability. In this way, in the support 2 manufactured by this process, the near end (the part close to the hard palate connecting end 1) is plastically deformable under an external force. Therefore, when the patient is induced to sleep, the lifting degree of the soft palate being supported may be adjusted within a certain range by adjusting the shape and degree of curvature of the implanted soft palate support under the monitor of an electronic laryngoscope, so as to achieve optimal treatment effect and comfort. The distal end of the support 2 still maintains good flexibility and restoring force, and particularly, the spring structure with complex patterns which is formed by laser engraving is wrapped and wound by the soft palate tissues, thereby enhancing the lifting force of the soft palate for restoring to the relaxed state of the soft palate during breathing.

In addition, surface modification is performed for the support 2 to improve the biocompatibility of the support 2, so as to facilitate penetration and growth of the soft palate tissues. One of the adopted methods is to spray various coatings, in which a biodegradable material may be coated, such as polylactic acid, polylactic acid-polyether copolymer, polycaprolactone, polycaprolactone-polyether block copolymer, polycaprolactone copolymer, polycaprolactone-polyether-polylactide copolymer, poly(glycolide-polylactide) copolymer, glycolide-L-lactide-caprolactone copolymer, polycaprolactone-polylactide-polyglycolide copolymer, and other fatty acid polylactone copolymer, and collagen, chitosan, gelatin, alginate natural polymer material, or a blend thereof; or a non-absorbable material may be coated, such as hydroxyapatite and various biological ceramics. In addition, it is also one of the effective methods to perform surface treatment for titanium and the titanium alloy, for example, plasma spraying is performed for titanium and the titanium alloy, a porous structure is manufactured on the surface, or a coating is manufactured by a magnetron sputtering method. See FIG. 59 and FIG. 60.

Embodiment 10

An Implanted Soft Palate Support of the Present Invention with an Elastic Module, which is a Spring Structure Coated with a Flexible Polymer Material The difference between this embodiment and Embodiment 9 lies in that, in this embodiment, the elastic module 20 is a spring structure coated with a flexible polymer material. During the manufacturing process, the tail portion of the support 2 is firstly connected with the rigid module 40 by using a coil spring, and then, the coil spring is coated with a flexible polymer material, so as to prevent tissue penetration and growth towards the inside of the coil spring. The soft palate tissues are driven by the rigid module 40 connected behind the elastic module 20. The rigid module 40 is made of a light porous material (such as porous polythene, porous polypropylene, and a titanium metal plate with through holes), so that the soft palate tissues may penetrate and grow on the rigid module, thereby increasing the bonding force between the soft palate tissues and the support. As such, during breathing, the elastic module of the support may generate an excellent restoring force to lift the soft palate tissues growing on and attached to the rigid module, so as to help the soft palate restore to a normal position when the soft palate relaxes, thereby preventing OSAHS and snoring from occurring. See FIG. 37 to FIG. 47.

Figures 39, 40:
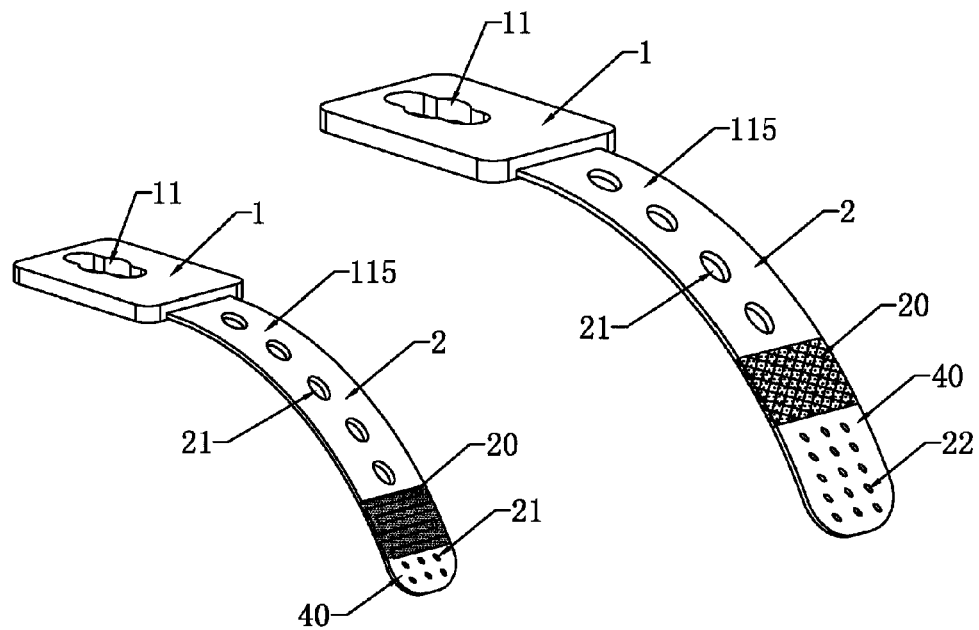
FIG. 39 is a schematic structural view of a combined-type implanted soft palate support of the present invention.
FIG. 40 is a schematic structural view of an implanted soft palate support of the present invention.

As shown in FIG. 39, the elastic module is manufactured by adopting the spring structure coated with the flexible polymer material. After being manufactured respectively, the hard palate connecting end and the support are assembled together. The spring structure serving as the elastic module 20 is formed from an elastic titanium alloy (such as a Nitinol alloy and titanium-zirconium-niobium superelastic alloy) plate by laser engraving, and then is coated with a medical flexible polymer material (such as a medical silica gel, polyurethane, or polytetrafluoroethylene film), thereby obtaining the elastic module 20. The elastic module 20 and the rigid module 40 are mounted on the tail portion of the support 2, so as to provide the tail portion of the support with good flexibility and an excellent restoring force after tensile deformation.

As shown in FIG. 40, the elastic module is manufactured by adopting a cross-grid type spring structure coated with the flexible polymer material. The spring structure is a cross-grid type spring structure braided by elastic alloy wires.

Figures 41, 42:
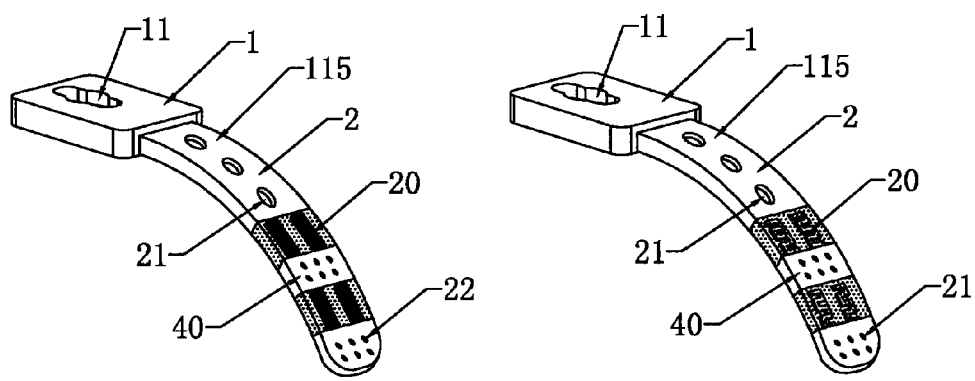
FIG. 41 is a schematic structural view of an implanted soft palate support of the present invention.
FIG. 42 is a schematic structural view of an implanted soft palate support of the present invention.
Figure 43:
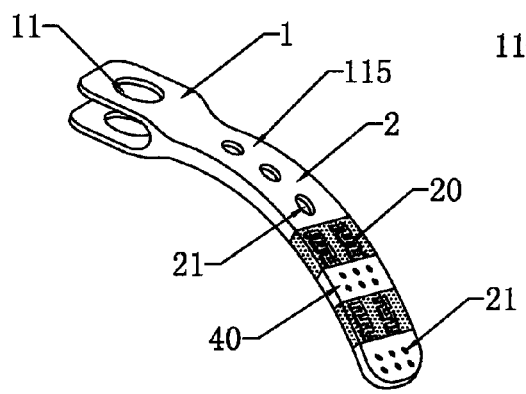
FIG. 43 is a schematic structural view of an implanted soft palate support of the present invention wherein the connecting structure of the hard palate connecting end is a U-shaped clamp structure for clamping onto a hard palate, and a fastener may be further used for reinforcement.
Figure 44:
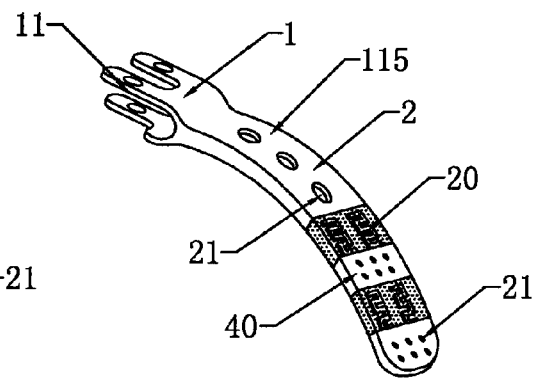
FIG. 44 is a schematic structural view of an implanted soft palate support of the present invention wherein the connecting structure of the hard palate connecting end is an epsilon-type U-shaped clamp structure for clamping onto a hard palate, and a fastener may be further used for reinforcement; and the degree of curvature of the support may be adjusted by bending the support to cause plastic deformation to the support, so as to control and adjust the lifting degree of a soft palate.

As shown in FIG. 41, the elastic module is manufactured by adopting a coil spring structure coated with a flexible polymer material. The coil spring is formed by winding a medical elastic alloy wire.

As shown in FIG. 42, the elastic module is manufactured by adopting a spring structure formed by laser engraving and coated with a flexible polymer material. The spring structure is formed from an elastic alloy plate by laser engraving.

Embodiment 11

An Implanted Soft Palate Support of the Present Invention when the Hard Palate Connecting End Adopts Different Connecting Structures The connecting structure 11 of the hard palate connecting end 1 has many different design solutions.

The simplest solution is to adopt through holes with different shapes, and the hard palate connecting end is connected with the hard palate 101 via a fastener 116. See FIG. 36 to FIG. 38 and FIG. 48 to FIG. 50.

Common fasteners 116 include, but are not limited to, a titanium bone nail, a titanium rivet, a titanium nut bolt structure, a titanium metal male and female engagement fastening structure, and various other fasteners.

The number of through holes on the hard palate connecting end 1 for positioning may be multiple, for example, two, three, or four. In principle, each implanted soft palate support of the present invention may be firmly fixed by using one through hole or two through holes at most.

In a clinical surgery, in order to adjust the lifting degree of the soft palate, the following methods may be adopted. First, the fixed position of the hard palate connecting end 1 is adjusted. Second, the degree of curvature of the support 2 is adjusted. Third, the length of the support 2 inserted into the soft palate 102 is adjusted. All the three methods can effectively adjust the lifting degree of the soft palate, so as to achieve an optimal treatment effect.

What is of particular interest is that, after surgery, when the patient is induced to sleep, the lifting degree of the soft palate being supported may be adjusted within a certain range by adjusting the shape and degree of curvature of the implanted soft palate support under the monitor of an electronic laryngoscope, so as to achieve an optimal treatment effect. Clinical application has proved that, the treatment method and the implanted instrument are popular with patients for treating OSAHS and snoring because of small wound, reliable efficacy, and great comfort.

The implanted soft palate support of the present invention may be made of any material capable of being implanted into the human body for a long term and has a certain force bearing function. Medical titanium metal and titanium alloys are preferred materials. Among the titanium alloys, a titanium-nickel shape memory alloy (such as the Nitinol alloy) is particularly suitable for manufacturing a tail portion of the support 2 because of pseudoelasticity and shape memory capability thereof, so as to meet the requirement that the tail portion of the support 2 needs to swing along with the soft palate 102; and may be designed into a fixed connecting structure 11 with a self-locking function because of shape memory characteristics thereof. In the embodiments shown in FIG. 45 to FIG. 47, the hard palate connecting end 1 may be made of a titanium-nickel shape memory alloy. In use, the connecting structure 11 of the hard palate connecting end 1 contracts in cold water (0° C.-15° C.), and after being passed through the through hole bored into the hard palate, the connecting structure 11 of the hard palate connecting end recovers to the geometrical shape set during the thermal setting process under the effect of body temperature, so that the implanted soft palate support of the present invention is firmly fixed to the hard palate.

The support 2 of the implanted soft palate support of the present invention has one or more through holes 21 or convex-concave lines or a rough surface 22, which may enhance the adhesion between the support 2 and soft palate tissues. The through holes 21 may be arranged in many different manners, and the convex-concave lines or rough surface 22 may also be designed in many ways.

In order to improve the biocompatibility of the implanted soft palate support of the present invention with human tissues, surface treatment may also be performed on the implanted soft palate support to manufacture a coating 24 capable of improving biocompatibility. One of the adopted methods is to spray various coatings, in which a biodegradable material may be coated, such as polylactic acid, polylactic acid-polyether copolymer, polycaprolactone, polycaprolactone-polyether block copolymer, polycaprolactone copolymer, polycaprolactone-polyether-polylactide copolymer, poly(glycolide-polylactide)copolymer, glycolide-L-lactide-caprolactone copolymer, polycaprolactone-polylactide-polyglycolide copolymer, and other fatty acid polylactone copolymer, and collagen, chitosan, gelatin, alginate natural polymer material, or a blend thereof; or a non-absorbable material may be coated, such as hydroxyapatite and various biological ceramics. In addition, it is also one of the effective methods to perform surface treatment for titanium and the titanium alloy, for example, plasma spraying is performed for titanium and the titanium alloy, a porous structure is manufactured on the surface, or a coating is manufactured by a magnetron sputtering method. See FIG. 56 and FIG. 60.

In order to increase the contact area of an edge of the implanted soft palate support of the present invention, and achieve an objective of blunting the edge, the edge of the support 2 may be wrapped with a thread (such as a titanium-nickel shape memory alloy wire, a polyester thread, a polyurethane thread, and other polymer material threads). As such, not only the edge effect of the support 2 is improved, the contact area of the edge is increased, and the objective of blunting the edge is achieved, but also the degree of curvature of the support 2 may be adjusted, and the support 2 has good flexibility. See FIG. 55.

Figure 45:
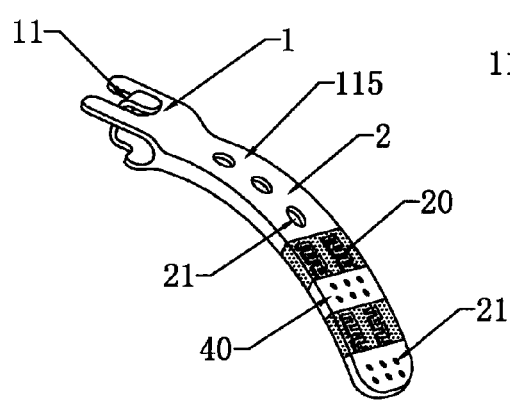
FIG. 45 is a schematic structural view of an implanted soft palate support of the present invention wherein the connecting structure of the hard palate connecting end is a lock cache structure used in such a manner that, during the surgery, a through hole is firstly bored into a hard palate, and a lock cache is passed through the through hole bored into the hard palate and then locked onto the hard palate, thereby forming a fixed structure; the degree of curvature of the support may be adjusted by bending the support to cause plastic deformation to the support, so as to control and adjust the lifting degree of a soft palate; wherein the connecting structure may be made of titanium, and more particularly may be made of a titanium-nickel shape memory alloy (Nitinol alloy) by configuring itself with a predefined geometrical shape when its temperature is higher than a recovery temperature according to shape memory characteristics of a shape memory alloy (usually a memory alloy with a recovery temperature between 20° C. and 33° C.), and during the surgery, the connecting structure of the hard palate connecting end is reduced in size by being put into cold water (0° C.-15° C.), and after being passed through the through hole bored into the hard palate, the connecting structure of the hard palate connecting end recovers to its predefined geometrical shape set during the thermal setting process because of the body temperature, so that the implanted soft palate support of the present invention is firmly fixed to the hard palate.
Figure 46:
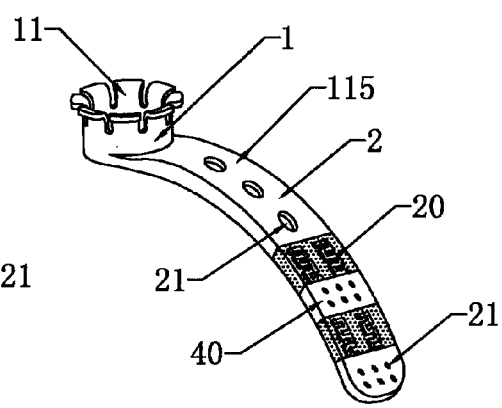
FIG. 46 is a schematic structural view of an implanted soft palate support of the present invention wherein the connecting structure of the hard palate connecting end is a rivet-type structure used in such a manner that, during the surgery, a through hole is firstly bored into a hard palate, a rivet is passed through the through hole bored into the hard palate, and then the hard palate connecting end is riveted to the hard palate using a special surgical tool, thereby forming a fixed structure; and the degree of curvature of the support may be adjusted by bending the support to cause plastic deformation to the support, so as to control and adjust the lifting degree of a soft palate.
Figure 47:
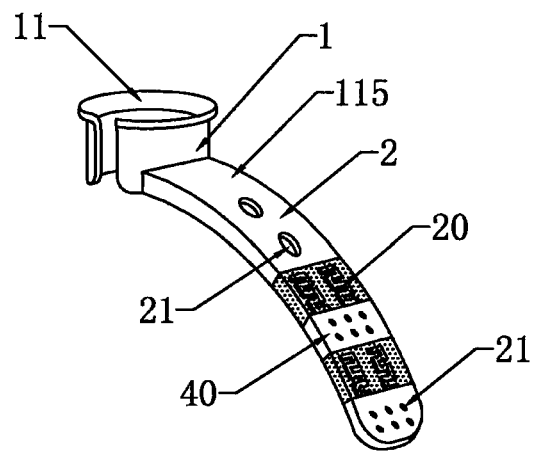
FIG. 47 is a schematic structural view of an implanted soft palate support of the present invention wherein the connecting structure of the hard palate connecting end is a self-expanding lock structure used in such a manner that, during the surgery, a through hole is firstly bored into a hard palate, and then the self-expanding lock structure is passed through the through hole bored into the hard palate, and thus the hard palate connecting end is fixed to the hard palate under an elastic restoring force; the degree of curvature of the support may be adjusted by bending the support to cause plastic deformation to the support, so as to control and adjust the lifting degree of a soft palate; and similar to the embodiment in FIG. 45, the embodiment in FIG. 47 may also be made of a titanium-nickel shape memory alloy for the convenience of implantation.
Figure 48:
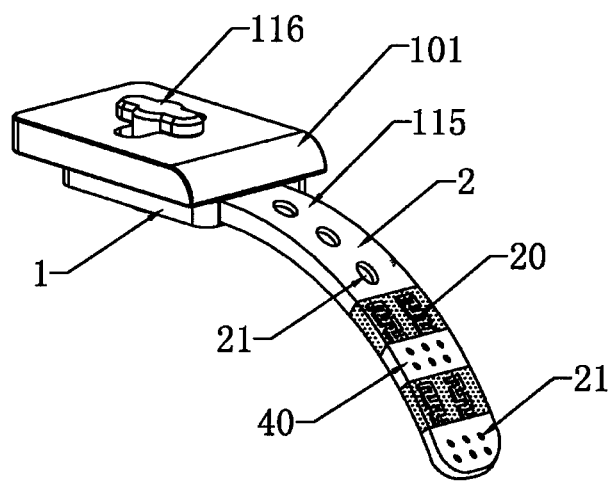
FIG. 48 is a schematic structural view of fixing an implanted soft palate support of the present invention to a hard palate using a T-shaped fastener.

The connecting structure 11 of the hard palate connecting end in FIG. 45 is a lock cache structure. The hard palate connecting end 1 is designed with a lock cache structure. In use, a through hole is firstly bored into the hard palate 101, and a lock cache 11 is passed through the through hole bored into the hard palate, and then locked to the hard palate 101, thereby forming a fixed structure bored into the hard palate. The degree of curvature of the support 2 may be adjusted by bending the support 2 to enable the support 2 to plastically deform, so as to control and adjust the lifting degree of the soft palate 102. This embodiment may be made of titanium metal, and more particularly may be made of a titanium-nickel shape memory alloy (Nitinol alloy). A required geometrical shape of a product above a recovery temperature is set according to shape memory characteristics of a shape memory alloy (usually a memory alloy with a recovery temperature between 20° C. and 33° C.). In use, the connecting structure 11 of the hard palate connecting end contracts in cold water (0° C.-15° C.), and after being passed through the through hole bored into the hard palate, the connecting structure 11 of the hard palate connecting end recovers to the geometrical shape set during the thermal setting process under the effect of body temperature, so that the implanted soft palate support of the present invention is firmly fixed to the hard palate.

Embodiment 12

An Implanted Soft Palate Support of the Present Invention with a Blunt Edge

In this embodiment, the edge of the support 2 is blunted with a medical polymer material thread 28. Holes or grooves 29 are firstly cut on the edge of the support before blunting, and then the edge of the support 2 is wrapped with a medical polymer material or medical polymer material thread 28 to form a blunt edge 23, so as to improve the edge effect of the support, increase the contact area of the edge, and achieve the objective of blunting the edge. See FIG. 55.

Embodiment 13

An Implanted Soft Palate Support of the Present Invention with a Biocompatible Coating In this embodiment, a biocompatible coating 24 is configured on the support 2, so as to enhance the bonding force between the support and the soft palate.

In order to improve the biocompatibility of the implanted soft palate support of the present invention with human tissues, surface treatment may be performed on the implanted soft palate support to manufacture a coating 24 capable of improving biocompatibility. One of the adopted methods is to spray various coatings, in which a biodegradable material may be coated, such as polylactic acid, polylactic acid-polyether copolymer, polycaprolactone, polycaprolactone-polyether block copolymer, polycaprolactone copolymer, polycaprolactone-polyether-polylactide copolymer, poly(glycolide-polylactide)copolymer, glycolide-L-lactide-caprolactone copolymer, polycaprolactone-polylactide-polyglycolide copolymer, and other fatty acid polylactone copolymer, and collagen, chitosan, gelatin, alginate natural polymer material, or a blend thereof; or a non-absorbable material may be coated, such as hydroxyapatite and various biological ceramics. In addition, it is also one of the effective methods to perform surface treatment for titanium and the titanium alloy, for example, plasma spraying is performed for titanium and the titanium alloy, a porous structure is manufactured on the surface, or a coating is manufactured by a magnetron sputtering method. See FIG. 56 and FIG. 60.

Embodiment 14

A Combined-Type Implanted Soft Palate Support of the Present Invention Capable of being Implanted in Stages The feature of this embodiment lies in that, the hard palate connecting end 1 and the support 2 may be clinically implanted in stages.

Firstly, the hard palate connecting end 1 is fixed to the hard palate 101 via a fastener 116. Three months later, the hard palate connecting end 1 will have been firmly fixed with the hard palate 101, and another surgery is performed, in which the support 2 is inserted into the soft palate 102, and at the same time, the near end of the support 2 and the hard palate connecting end 1 are connected together through convex-concave engagement or a fastener (see FIG. 51 to FIG. 52 and FIG. 49 to FIG. 50). The advantage lies in that the hard palate connecting end 1 and the hard palate 102 are firmly connected, and the disadvantage lies in that it is necessary to perform two surgeries, which increases the medical expense of the patient.

In the combined-type implanted soft palate support of the present invention, the hard palate connecting end 1 and the support 2 that are implanted in stages may be combined through convex-concave engagement (see FIG. 51 to FIG. 52) or fastener connection (see FIG. 53 and FIG. 54). Definitely, many different specific implementations may be further proposed according to the technical solution of the present invention.

Embodiment 15

Figure 61:
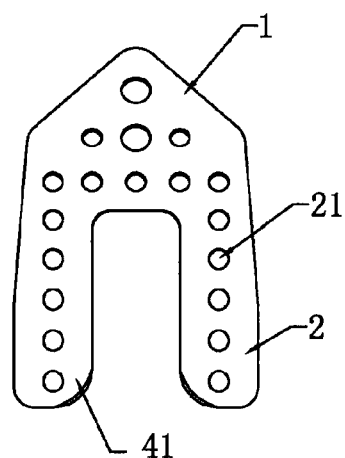
FIG. 61 is a schematic structural view of a U-shaped implanted soft palate support of the present invention, wherein there are a pair of symmetric small chamfers near the distal ends of the support of the implanted soft palate support, and the small chamfers tilt backwards such that its curvature is adapted to the movement of an uvula; and the U-shaped implanted soft palate support of the present invention is particularly suitable for treating patients with serious OSAHS, and in this case, the soft palate support is implanted deeply into the soft palate so as to lift a large area of the soft palate.
Figure 62:
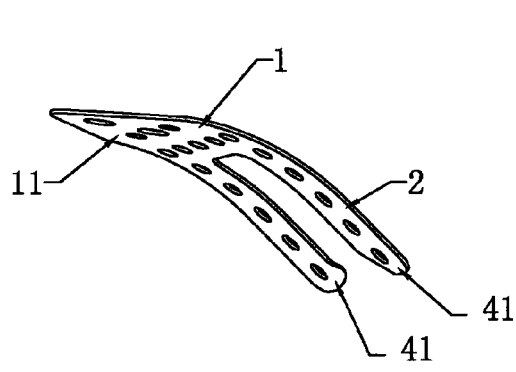
FIG. 62 is a schematic structural front view of FIG. 61.
Figure 63:
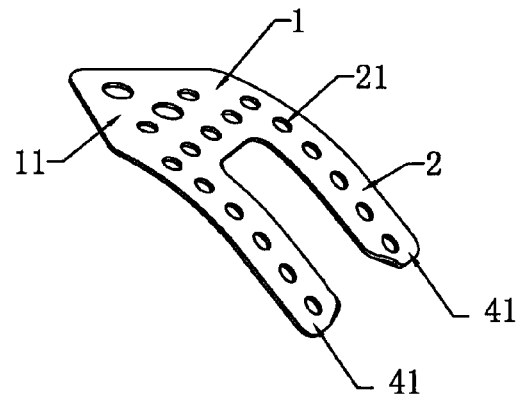
FIG. 63 is a schematic structural back view of FIG. 61.

An Implanted Soft Palate Support of the Present Invention for Serious OSAHS Patients For serious OSAHS patients, since the soft palate seriously collapses, a large lifting force and a large lifting area are required to achieve a good treatment effect. In this embodiment, an implanted soft palate support of the present invention capable of being deeply inserted into the soft palate and having a large lifting area and a large lifting force is particularly designed. The basic structure of this embodiment is similar to that of the fork-shaped implanted soft palate support of the present invention shown in FIG. 6 (see FIG. 30 and FIG. 31), and the difference lies in that this embodiment has a larger area. Further, since the support is deeply inserted into the soft palate and is close to a uvula, in order to adapt to the swing of the uvula, the tail portion of the support of this embodiment is designed with small chamfers 41 matching with the swing of the uvula. See FIG. 61 to FIG. 63. The small chamfers 41 can ensure large supporting and lifting forces of the implanted soft palate support of the present invention without affecting the swing of the uvula; therefore, the implanted soft palate support of this embodiment is particularly suitable for treatment of serious OSAHS patients.

Embodiment 16

Figure 64:
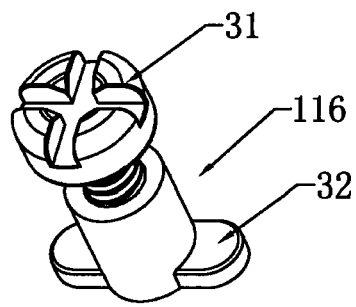
FIG. 64 is a schematic structural view of a screw-nut T-shaped fastener which is used to fix an implanted soft palate support of the present invention.
Figure 65:
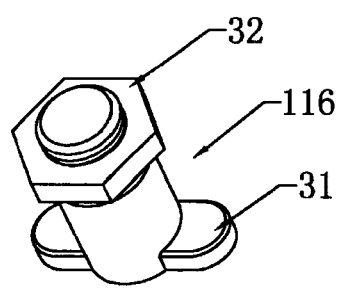
FIG. 65 is a schematic structural view of a nut-bolt T-shaped fastener which is used to fix an implanted soft palate support of the present invention.
Figure 66:
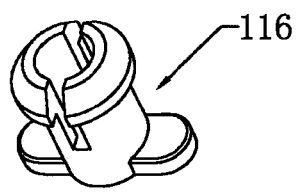
FIG. 66 is a schematic structural view of a single-cut T-shaped fastener for convex-concave engagement which is used to fix an implanted soft palate support of the present invention.
Figure 67:
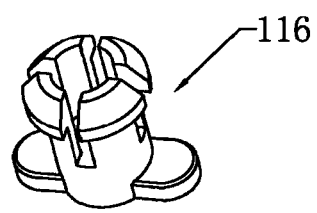
FIG. 67 is a schematic structural view of a double-cut T-shaped fastener for convex-concave engagement which is used to fix an implanted soft palate support of the present invention.

An Implantation Method for Implanting and Fixing the Implanted Soft Palate Support of the Present Invention by Using a T-Shaped Fastener In this embodiment, a special T-shaped fastener for fixing the implanted soft palate support of the present invention to the hard palate 101 and a method for implanting and fixing the implanted soft palate support of the present invention are described. The T-shaped fastener may be of a convex-concave engagement type or a thread type, and includes: a simple T-shaped structure with a cylindrical core pin, in which an upper end of the T-shaped structure fastener may have a nut or a screw for tightly pressing the implanted soft palate support 115 onto the hard palate 101 (the thread type, see FIG. 64 and FIG. 65); or a T-shaped structure fastener halved by one cut (the convex-concave engagement type, see FIG. 66), or a T-shaped structure fastener quartered by two cuts (the convex-concave engagement type, see FIG. 67), which may tightly press the implanted soft palate support 115 of the present invention onto the hard palate 101 directly through convex-concave engagement without tightly screwing the nut or the screw. In use, a rectangular through hole matching with the T-shaped fastener is firstly opened on the hard palate 101, and the T-shaped fastener 116 is passed through a rectangular through hole 11 matching with the T-shaped fastener on the hard palate connecting end 1 and the rectangular through hole on the hard palate 101, rotated by 90 degrees, and then screwed tightly with the nut, thereby tightly pressing the implanted soft palate support 115 of the present invention onto the hard palate 101; or the T-shaped fastener is rotated by 90 degrees, so as to achieve engagement between the halved T-shaped structure fastener or the quartered T-shaped fastener and the rectangular through hole 11 matching with the T-shaped fastener on the hard palate connecting end 1, thereby tightly pressing the implanted soft palate support 115 of the present invention onto the hard palate 101. See FIG. 48 to FIG. 50. Such a T-shaped fastener has the advantage of small wound, and the implanted soft palate support 115 of the present invention may be firmly fixed to the hard palate 101 simply in a single direction along the oral cavity.

In addition, the thread-type T-shaped fastener adopts a nut bolt structure, which is particularly suitable for fixing the implanted soft palate support 115 of the present invention to plate-like bone tissues such as the hard palate 101. The screw thread of the T-shaped fastener is between metal pieces or plastic pieces, which overcomes the defect that an ordinary titanium bone nail cannot be easily fixed to the hard palate 101 with a screw because the hard palate 101 is too thin.

It should be noted that, the structures disclosed and described in the present invention may be replaced by other structure with the same effect, and the embodiments described in the present invention are not intended to limit the present invention. Though the preferred embodiments of the present invention have been introduced and described in the specification, persons skilled in this field should know that these embodiments are merely described by way of example, and persons skilled in this field may make various changes, improvements, and replacements without departing from the

What is claimed is:

1. An implanted soft palate support, being a flat implant made of a material capable of being implanted into a human body for a long term period of time, comprising:
   a hard palate connecting end having a connecting structure configured to be connected with a hard palate; and
   a support, being a flat implant capable of being inserted into a soft palate, wherein the support is a flat implant formed by a chip and a spring wire,
   wherein the hard palate connecting end and the support are fixedly connected, or detachably connected.

2. The implanted soft palate support according to claim 1, wherein the connecting structure on the hard palate connecting end is one selected from the following structures: a hole structure, a U-shaped clamp structure, a lock cache structure, a rivet-type structure, and a self-expanding lock structure.

3. The implanted soft palate support according to claim 1, wherein the support is selected from flat implants having one of the following structures: a strip-shaped structure, a plate-shaped structure, a bar-shaped structure, and a net-shaped structure.

4. The implanted soft palate support according to claim 1, wherein the support has a radian matching a curvature of the soft palate of human body when it relaxes.

5. The implanted soft palate support according to claim 1, wherein the support has one or more through holes.

6. The implanted soft palate support according to claim 1, wherein the support has one or more convex-concave lines.

7. The implanted soft palate support according to claim 1, wherein an edge of the support is a blunt edge formed by blunting.

8. The implanted soft palate support according to claim 7, wherein the edge of the support is a blunt edge coated with a flexible polymer material.

9. The implanted soft palate support according to claim 1, wherein the support has a coating capable of improving biocompatibility.

10. The implanted soft palate support according to claim 1, wherein the implanted soft palate support is made of at least one of the following materials capable of being implanted into the human body for a long term: a metal material, a medical polymer material, and a medical biodegradable material, wherein the metal material is selected from a group consisting of titanium, a titanium alloy, and a titanium-nickel shape memory alloy.

11. The implanted soft palate support according to claim 1, wherein the support comprises an elastic module, and the elastic module is an object deformable under an external force and shape-recoverable or substantially shape-recoverable after the external force is removed.

12. The implanted soft palate support according to claim 11, wherein the elastic module is selected from one of the following structures: an elastic polymer material sheet or strip, a spring structure, and a spring structure coated with a flexible polymer material.

13. The implanted soft palate support according to claim 11, wherein the support further comprises a rigid module, and the rigid module is an object plastically deformable under an external force and not shape-recoverable after the external force is removed.

14. The implanted soft palate support according to claim 11, wherein the support further includes one or more through holes or a convex-concave surface or rough surface supporting tissue penetration and growth.

15. An implanted soft palate support, being a flat implant made of a material capable of being implanted into a human body for a long term period of time, comprising:
   a hard palate connecting end having a connecting structure configured to be connected with a hard palate; and
   a support, being a flat implant capable of being inserted into a soft palate, wherein the support is a flat implant braided by elastic wires,
   wherein the hard palate connecting end and the support are fixedly connected, or detachably connected.

16. An implantation method of an implanted soft palate support, the implanted soft palate support including a hard palate connecting end having a connecting structure and a flat implant support formed by a chip and a spring wire, wherein the hard palate connecting end and the support are fixedly connected, or detachably connected, the method comprising: fixing the hard palate connecting end of the implanted soft palate support to a hard palate using a fastener, and inserting the support of the implanted soft palate support into a soft palate.

17. The implantation method according to claim 16, wherein the support is inserted into the soft palate by a length equal to 1/5 to 4/5, and most preferably, 2/3 to 3/4, of a total length of the soft palate.

* * * * *